(12) United States Patent
McAuliffe et al.

(10) Patent No.: US 8,691,541 B2
(45) Date of Patent: Apr. 8, 2014

(54) BIOLOGICAL PRODUCTION OF PENTOSE SUGARS USING RECOMBINANT CELLS

(75) Inventors: Joseph C. McAuliffe, Sunnyvale, CA (US); Rachel E. Muir, Redwood City, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 13/335,792

(22) Filed: Dec. 22, 2011

(65) Prior Publication Data

US 2012/0329102 A1    Dec. 27, 2012

Related U.S. Application Data

(60) Provisional application No. 61/426,483, filed on Dec. 22, 2010.

(51) Int. Cl.
*C12N 1/12* (2006.01)

(52) U.S. Cl.
USPC .......... 435/167; 435/107; 435/252.3

(58) Field of Classification Search
USPC .................................. 435/167, 243
See application file for complete search history.

(56) References Cited

U.S. PATENT DOCUMENTS

| | | |
|---|---|---|
| 4,570,029 A | 2/1986 | Kulprathipanja et al. |
| 4,683,202 A | 7/1987 | Mullis |
| 4,703,007 A | 10/1987 | Mulholland et al. |
| 5,849,970 A | 12/1998 | Fall et al. |
| 5,874,276 A | 2/1999 | Fowler et al. |
| 6,022,725 A | 2/2000 | Fowler et al. |
| 6,106,888 A | 8/2000 | Dale et al. |
| 6,176,176 B1 | 1/2001 | Dale et al. |
| 6,268,328 B1 | 7/2001 | Mitchinson et al. |
| 6,316,695 B1 | 11/2001 | Han et al. |
| 6,998,471 B2 | 2/2006 | Hallahan et al. |
| 7,129,392 B2 | 10/2006 | Hahn et al. |
| 7,132,527 B2 | 11/2006 | Payne et al. |
| 7,241,587 B2 | 7/2007 | Dodge et al. |
| 7,262,041 B2 | 8/2007 | Baldwin et al. |
| 7,659,097 B2 | 2/2010 | Renninger et al. |
| 8,173,410 B2 | 5/2012 | Bott et al. |
| 2005/0079617 A1 | 4/2005 | Cervin et al. |
| 2005/0287625 A1 | 12/2005 | Miller, Jr. et al. |
| 2008/0038805 A1 | 2/2008 | Melis |
| 2008/0274523 A1 | 11/2008 | Renninger et al. |
| 2009/0137014 A1 | 5/2009 | Tsuruta et al. |
| 2009/0203102 A1 | 8/2009 | Cervin et al. |
| 2009/0282545 A1 | 11/2009 | Eichelberger et al. |
| 2010/0048964 A1 | 2/2010 | Calabria et al. |
| 2010/0086978 A1 | 4/2010 | Beck et al. |
| 2010/0113846 A1 | 5/2010 | McAuliffe et al. |
| 2010/0167370 A1 | 7/2010 | Chotani et al. |
| 2010/0167371 A1 | 7/2010 | Chotani et al. |
| 2010/0178679 A1 | 7/2010 | Anthony et al. |
| 2010/0184178 A1 | 7/2010 | Beck et al. |
| 2010/0297749 A1 | 11/2010 | Aravanis et al. |
| 2011/0014672 A1 | 1/2011 | Chotani et al. |
| 2011/0045563 A1 | 2/2011 | Melis |
| 2011/0178261 A1 | 7/2011 | Feher et al. |
| 2012/0164711 A1 | 6/2012 | Muir et al. |

FOREIGN PATENT DOCUMENTS

| | | |
|---|---|---|
| EP | 0 215 594 A2 | 3/1987 |
| EP | 0 215 594 A3 | 3/1987 |
| EP | 0 215 594 B1 | 3/1987 |
| EP | 0 215 594 B2 | 3/1987 |
| EP | 0 238 023 A2 | 9/1987 |
| EP | 0 238 023 A3 | 9/1987 |
| EP | 0 238 023 B1 | 9/1987 |
| EP | 0 238 023 B2 | 9/1987 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| WO | WO-95/04134 A1 | 2/1995 |
| WO | WO-96/35796 A1 | 11/1996 |
| WO | WO-98/02550 A2 | 1/1998 |
| WO | WO-98/02550 A3 | 1/1998 |
| WO | WO-2009/132220 A3 | 10/2002 |
| WO | WO-2004/033646 A2 | 4/2004 |
| WO | WO-2004/033646 A3 | 4/2004 |
| WO | WO-2005/001036 A2 | 1/2005 |
| WO | WO-2005/001036 C1 | 1/2005 |
| WO | WO-2008/003078 A2 | 1/2008 |
| WO | WO-2008/003078 A3 | 1/2008 |
| WO | WO-2008/003078 A8 | 1/2008 |
| WO | WO-2008/128159 A1 | 10/2008 |
| WO | WO-2009/041581 A1 | 4/2009 |
| WO | WO-2009/076676 A2 | 6/2009 |
| WO | WO-2009/076676 A3 | 6/2009 |
| WO | WO-2009/079448 A2 | 6/2009 |
| WO | WO-2009/079448 A3 | 6/2009 |

(Continued)

OTHER PUBLICATIONS

Devos et al., Proteins: Structure, Function and Genetics, 2000, vol. 41: 98-107.*

(Continued)

*Primary Examiner* — Tekchand Saidha
*Assistant Examiner* — Rama P Ramanujam
(74) *Attorney, Agent, or Firm* — Morrison & Foerster LLP

(57) ABSTRACT

The invention provides, inter alia, compositions and methods for the biological production of pentose sugars, such as 2-methylerythritol (2-ME), 1-deoxyxylulose (1-DX), and monoacetylated-2-C-methylerythritols, using recombinant cells.

22 Claims, 4 Drawing Sheets

(56) References Cited

FOREIGN PATENT DOCUMENTS

| WO | WO-2009/132220 A2 | 10/2009 |
|---|---|---|
| WO | WO-2010/003007 A2 | 1/2010 |
| WO | WO-2010/003007 A3 | 1/2010 |
| WO | WO-2010/031062 A1 | 3/2010 |
| WO | WO-2010/031068 A1 | 3/2010 |
| WO | WO-2010/031076 A2 | 3/2010 |
| WO | WO-2010/031076 A3 | 3/2010 |
| WO | WO-2010/031077 A1 | 3/2010 |
| WO | WO-2010/031079 A1 | 3/2010 |
| WO | WO-2010/078457 A2 | 7/2010 |
| WO | WO-2010/078457 A3 | 7/2010 |
| WO | WO-2010/124146 A2 | 10/2010 |
| WO | WO-2010/124146 A3 | 10/2010 |
| WO | WO-2010/148150 A1 | 12/2010 |
| WO | WO-2010/148256 A1 | 12/2010 |
| WO | WO-2011/034863 A1 | 3/2011 |
| WO | WO-2012/058494 A2 | 5/2012 |
| WO | WO-2012/058494 A3 | 5/2012 |
| WO | WO-2012/088450 A1 | 6/2012 |
| WO | WO-2012/088462 A1 | 6/2012 |

OTHER PUBLICATIONS

Whisstock et al., Prediction of protein function from protein sequence and structure. Quarterly Reviews of Biophysics 2003, vol. 36 (3): 307-340.*

Witkowski et al., Conversion of a â-Ketoacyl Synthase to a Malonyl Decarboxylase by Replacement of the Active-Site Cysteine with Glutamine Biochemistry. 38:11643-11650, 1999.*

Wishart et al., A Single Mutation Converts a Novel Phosphotyrosine Binding Domain into a Dual-specificity Phosphatase J. Biol. Chem., 1995, vol. 270 (10): 26782-26785.*

Broun et al., Catalytic Plasticity of Fatty Acid Modification Enzymes Underlying Chemical Diversity of Plant Lipids Science 282:1315-1317, 1998.*

Kisselev. Polypeptide Release Factors in Prokaryotes and Eukaryotes: Same Function, Different Structure. Structure, 2002, vol. 10: 8-9.*

Seffernick et al., Melamine Deaminase and Atrazine Chlorohydrolase: 98 Percent Identical but Functionally Different. J. Bacteriol. 183(8): 2405-2410, 2001.*

Chica et al., Semi-rational approaches to engineering enzyme activity: combining the benefits of directed evolution and rational design. Curr. Opin. Biotechnol., 2005, vol. 16: 378-384.*

Sen et al., Developments in Directed Evolution for Improving Enzyme Functions. Biochem. Biotechnol., 2007, Vol.143: 212-223.*

Kimchi-Sarfaty et al., A "Silent" Polymorphism in the MDR1 Gene Changes Substrate Specificity. Science, 2007, vol. 315: 525-528.*

Nackley et al., Human Catechol-O-Methyltransferase Haplotypes Modulate Protein Expression by Altering mRNA Secondary Structure. Science, 2006, vol. 314: 1930-1933.*

Sauna et al., Silent Polymorphisms Speak: How They Affect Pharmacogenomics and the Treatment of Cancer. Cancer Res., 2007, vol. 67: 9609-9612.*

Grawert et al., IspH Protein of *Escherichia coli*: Studies on Iron-Sulfur Cluster Implementation and Catalysis. JACS., 2004, vol. 126; 12847-12855.*

Puan et al., fldA is an essential gene required in the 2-C-methyl-D-erythritol 4-phosphate pathway for isoprenoid biosynthesis. FEBS Lett, 2005, vol. 579: 3802-3806.*

Zepeck et al., Biosynthesis of Isoprenoids. Purification and Properties of IspG Protein from *Escherichia coli*. J. Org. Chem., 2005, vol. 70: 9168-9174.*

Sangari et al., PNAS | A new family of enzymes catalyzing the first committed step of the methylerythritol 4-phosphate (MEP) pathway for isoprenoid biosynthesis in bacteria. Aug. 10, 2010 | vol. 107 | No. 32 | 14081-14086.*

Singh et al., Current Pharmaceutical Design. Targeting the Methyl Erythritol Phosphate (MEP) Pathway for Novel Antimalarial, Antibacterial and Herbicidal Drug Discovery: Inhibition of 1-Deoxy-D-Xylulose-5-Phosphate Reductoisomerase (DXR) Enzyme. 2007, 13, 1161-1177.*

Rodriguez-Concepcion et al., Plant Physiology. Elucidation of the Methylerythritol Phosphate Pathway for Isoprenoid Biosynthesis in Bacteria and Plastids. A Metabolic Milestone Achieved through Genomics. Plant Physiol. Nov. 2002, vol. 130, pp. 1079-1089.*

Akhtar, M.K. et al. (2008). "Deletion of iscR Stimulates Recombinant Clostridial Fe-Fe Hydrogenase Activity and $H_2$-accumulation in *Escherichia coli* BL21 (DE3)," *Applied Microbiol. Biotechnol.* 78(5):853-862.

Anderson, M.S. et al. (Nov. 15, 1989). "Isopentenyl Diphosphate: Dimethylallyl Diphosphate Isomerase. An Improved Purification of the Enzyme and Isolation of the Gene From *Saccharomyces cerevisiae*," *J. Biol. Chem.* 264(32):19169-19175.

Baba, T. et al. (2006). "Construction of *Escherichia coli* K-12 In-Frame, Single-Gene Knockout Mutants: The Keio Collection," *Mol. Syst. Biol.*, 2006.0008:1-11.

Bellion, E. et al. (1993). "Methylamine Utilization in Yeast and Bacteria: Studies Using in vivo NMR," Chapter 32 in *Microbial Growth on $C_1$ Compounds*, Muerrell, J.C. et al. eds, Intercept Ltd: Andover, UK, pp. 415-432.

Bennett, J.W. et al. eds. (1991). "Gene Cloning and Analysis," Chapter 3 in *More Gene Manipulations in Fungi*, Academic Press, San Diego, CA pp. 70-76.

Berka, R.M. et al. (1989). "The Development of Gene Expression Systems for Filamentous Fungi," *Biotechnology Advances* 7(2):127-154.

Bhayana, V. et al. (Jun. 1984). "Amino Acid Sequence of *Escherichia coli* Citrate Synthase," *Biochemistry* 23(13):2900-2905.

Bitoun, J.P. et al. (Dec. 2008). "*Escherichia coli* FtnA Acts as an Iron Buffer for Re-assembly of Iron-Sulfur Clusters in Response to Hydrogen Peroxide Stress," *Biometals* 21(6):693-703.

Boel, E. et al. (1984). "Two Different Types of Intervening Sequences in the Glucoamylase Gene from *Aspergillus niger*," *The EMBO Journal* 3(7):1581-1585.

Bologna, F.P. et al. (Aug. 2007). "*Escherichia coli* Malic Enzymes: Two Isoforms with Substantial Differences in Kinetic Properties, Metabolic Regulation, and Structure," *Journal of Bacteriology* 189(16):5937-5946.

Bouvier, F. et al. (2005). "Biogenesis, Molecular Regulation and Function of Plant Isoprenoids," *Progress in Lipid Res.* 44:357-429.

Broun, P. et al. (Nov. 13, 1998). "Catalytic Plasticity of Fatty Acid Modification Enzymes Underlying Chemical Diversity of Plant Lipids," *Science* 282:1315-1317.

Brown, L. et al. (Aug. 26, 1996). "Enzymatic Saccharification of Lignocellulosic Biomass," *NREL, Ethanol Project, Chemical Analysis and Testing Task, LAP-009*, pp. 1-8.

Bukau, B. et al. (Feb. 6, 1998). "The Hsp70 and Hsp60 Chaperone Machines," *Cell* 92:351-366.

Bunch, P.K. et al. (1997). "The *IdhA* Gene Encoding the Fermentative Lactate Dehydrogenase of *Escherichia coli*," *Microbiology* 143:187-195.

Campbell, E.I. et al. (1989). "Improved Transformation Efficiency of *Aspergillus niger* Using the Homologus niaD Gene for Nitrate Reductase," *Curr. Genet.* 16:53-56.

Cao, Q-N. et al. (2000). "Penicillopepsin-JT2, a Recombinant Enzyme from *Penicillium janthinellum* and the Contribution of a Hydrogen Bond in Subsite $S_3$ to $k_{cat}$," *Protein Science* 9:991-1001.

Chao, Y-P. et al. (2002). "Stringent Regulation and High-Level Expression of Heterologous Genes in *Escherichia coli* Using T7 System Controllable by the araBAD Promoter," *Biotechnol. Prog.* 18(2):394-400.

Chen, J-S. et al. (Feb. 1979). "A Simple Hydrogenase-Linked Assay for Ferredoxin and Flavodoxin," *Analytical Biochemistry* 93(1):216-222.

Chica, R.A. et al. (2005, e-pub Jul. 1, 2005). "Semi-Rational Approaches to Engineering Enzyme Activity: Combining the Benefits of Directed Evolution and Rational Design," *Current Opinion in Biotechnology* 16:378-384.

Cirino, P.C. et al. (Dec. 20, 2006, e-pub Jul. 12, 2006). "Engineering *Escherichia coli* for Xylitol Production From Glucose-Xylose Mixtures," *Biotechnology and Bioengineering* 95(6):1167-1176.

(56) References Cited

OTHER PUBLICATIONS

Devos, D. et al. (2000). "Practical Limits of Function Prediction," *Proteins: Structure, Function, and Genetics* 41:98-107.
Dhe-Paganon, S. et al. (1994). "Mechanism of Mevalonate Pyrophosphate Decarboxylase: Evidence for a Carbocationic Transition State," *Biochemistry* 33(45):13355-13362.
Djaman, O. et al. (Oct. 22, 2004). "Repair of Oxidized Iron-Sulfur Clusters in *Escherichia coli*," *J. of Biol. Chem.* 279(43):44590-44599.
Duckworth, H.W. et al. (1987). "Structural Basis for Regulation in Gram-Negative Bacterial Citrate Synthases," *Biochem. Soc. Symp.* 54:83-92.
Ecocyc. (2005) "ribF-ileS-IspA-fkpB-ispH 5-gene operon," located at <http://ecocyc.org/ECOLI/substring-search?type=NIL&object-+ribF-ileS-IspA-fkpB-ispH+,> last visited on May 29, 2012, three pages.
Eppler, T. et al. (1999). "Glycerol-3-Phosphate-Mediated Repression of *malT* in *Escherichia coli* Does Not Require Metabolism, Depends on Enzyme IIA$^{Glc}$ and is Mediated by cAMP Levels," *Molecular Microbiology* 33(6):1221-1231.
Finkelstein, D.B. (1992). "Transformation," Chapter 6 in *Biotechnology of Filamentous Fungi*, Butterworth-Heinemann: Boston, MA, pp. 113-156.
Fraenkel, D.G. (Apr. 1968). "Selection of *Escherichia coli* Mutants Lacking Glucose-6-Phosphate Dehydrogenase or Gluconate-6-Phosphate Dehydrogenase," *J. Bacteriol.* 95(4):1267-1271.
GenBank Accession No. AAQ84170, last updated on Feb. 15, 2005, located at < http://www.ncbi.nlm.nih.gov/protein/AAQ84170>, last visited on Dec. 22, 2011, 2 pages.
GenBank Accession No. AJ457070, last updated on Apr. 15, 2005, located at <http://www.ncbi.nlm.nih.gov/nuccore/38092202>, last visited on Jun. 2, 2010, 2 pages.
GenBank Accession No. AY182241, last updated on May 4, 2004, located at <http://www.ncbi.nlm.nih.gov/nuccore/32265057>, last visited on Jun. 2, 2010, 2 pages.
GenBank Accession No. AY279379, last updated on Mar. 11, 2005, located at <http://www.ncbi.nlm.nih.gov/nuccore/30984014>, last visited on Jun. 2, 2010, 2 pages.
GenBank Accession No. AY316691, last updated on Feb. 15, 2005, located at <http://www.ncbi.nlm.nih.gov/nuccore/35187003>, last visited on Jun. 2, 2010, 2 pages.
GenBank Accession No. AY341431, last updated on Feb. 15, 2005, located at <http://www.ncbi.nlm.nih.gov/nuccore/AY341431>, last visited on Feb. 27, 2012, 2 pages.
GenBank Accession No. CAC35696, last updated Apr. 15, 2005, located at <http://www.ncbi.nlm.nih.gov/protein/CAC35696>, last visited on Nov. 1, 2011, 1 page.
GenBank Accession No. CP001164, last updated Dec. 14, 2011, located at <http://www.ncbi.nim.nih.gov/protein/CP001164> last visted on May 29, 2012, seventy-six pages.
GenBank Accession No. D86235, last updated Oct. 29, 1997, located at <http://www.ncbi.nlm.nih.gov/nuccore/D86235> last visited on Feb. 27, 2012, two pages.
GenBank Accession No. E02927, last updated Nov. 4, 2005, located at <http://www.ncbi.nlm.nih.gov/nuccore/E02927> last visited on May 29, 2012, one page.
GenBank Accession No. NC_001416, last updated Mar. 11, 2011, located at <http://www.ncbi.nlm.nih.gov/nuccore/NC_001416> last visited on Feb. 8, 2013, forty-two pages.
GenomeNet (2012). "Steroid Biosynthesis—Reference Pathway," in KEGG: Kyoto Encyclopedia of Genes and Genomes, located at <http://www.genome.jp/kegg/pathway/map/map00100.html>, last visited on Dec. 28, 2012, 1 page.
Goedegebuur, F. et al. (2002, e-pub May 7, 2002). "Cloning and Relational Analysis of 15 Novel Fungal Endoglucanases from Family 12 Glycosyl Hydrolase," *Curr. Genet.* 41:89-98.
Grävert, T. et al. (Oct. 13, 2004, e-pub. Sep. 21, 2004). "IspH Protein of *Escherichia coli*: Studies on Iron-Sulfur Cluster Implementation and Catalysis," *J. Am. Chem. Soc.* 126(40):12847-12855.

Greenberg, J.P. et al. (1993). "Sub-Parts Per Billion Detection of Isoprene Using a Reduction Gas Detector with a Portable Gas Chromatograph," *Atmospheric Environment* 27A(16):2689-2692.
Guzman, L.M. et al. (Jul. 1995). "Tight Regulation, Modulation, and High-Level Expression by Vectors Containing the Arabinose PBAD Promoter," *Journal of Bacteriology* 177(14):4121-4130.
Harkki, A. et al. (Jun. 1989). "A Novel Fungal Expression System: Secretion of Active Calf Chymosin from the Filamentous Fungus *Trichoderma Reesei*," *Bio/Technology* 7:596-603.
Harkki, A. et al. (Mar. 1991). "Genetic Engineering of *Trichoderma* to Produce Strains with Novel Cellulase Profiles," *Enzyme Microb. Technol.* 13:227-233.
Hedl, M. et al. (Apr. 2002). "*Enterococcus faecalis* Acetoacetyl-Coenzyme A Thiolase/3-Hydroxy-3-Methyglutaryl-Coenzyme A Reductase, a Dual-Function Protein of Isopentenyl Diphosphate Biosynthesis," *J. Bacteriol.* 184(8):2116-2122.
Hoeffler, J-F. et al. (Sep. 2002). "Isoprenoid Biosynthesis via the Methylerythritol Phosphate Pathway. Mechanistic Investigations of the 1-deoxy-D-xylulose 5-phosphate Reductoisomerase," *Eur. J. Biochem.* 269(18):4446-4457.
Hunter, B.K. (1985). "Formaldehyde Metabolism by *Escherichia coli*. Carbon and Solvent Deuterium Incorporation into Glycerol, 1,2-Propanediol, and 1,3-Propanediol," *Biochemistry* 24(15):4148-4155.
Ilmén, M. et al. (Apr. 1997). "Regulation of Cellulase Gene Expression in the Filamentous Fungus *Trichoderma reesei*," *Appl. Environ. Microbiol.* 63(4):1298-1306.
Innis, M.A. et al. (Apr. 1985). "Expression, Glycosylation, and Secretion of an *Aspergillus* Glucoamylase by *Saccharomyces cerevisiae*," *Science* 228:21-26.
International Search Report mailed on Sep. 9, 2010, for PCT Patent Application No. PCT/US2010/038904, filed Jun. 16, 2010, published on Dec. 23, 2010, as WO 2010/148150, 3 pages.
International Search Report mailed on Mar. 2, 2012, for PCT Patent Application No. PCT/US2011/066924, filed on Dec. 22, 2011, published on Jun. 28, 2012 as WO 2012/088450, 3 pages.
International Search Report mailed on May 18, 2012, for PCT Patent Application No. PCT/US2011/066949, filed on Dec. 22, 2011, published on Jun. 28, 2012, as WO 2012/088462, 3 pages.
Iwakura, M. et al. (1979). "Studies on Regulatory Functions of Malic Enzymes," *J. Biochem.* 85:1355-1365.
Jawaid, S. et al. (Dec. 14, 2009). "Kinetic Characterization and Phosphoregulation of the *Francisella tularensis* 1-Deoxy-D-Xylulose 5-Phosphate Reductoisomerase (MEP Synthase)," *PLoS ONE* 4(12):e8288, 9 pages.
Jobling, M.G. et al. (Jul. 17, 1990). "Construction of Vectors with the p15a Replicon, Kanamycin Resistance, Inducible *lacZα* and pUC18 or pUC19 Multiple Cloning Sites," *Nucleic Acids Research* 18(17):5315-5316.
Julsing, M.K. et al. (Jul. 2007, e-pub Apr. 26, 2007) "Functional Analysis of Genes Involved in the Biosynthesis of Isoprene in *Bacillus subtilis*," *Appl. Microbiol. Biotechnol.* 75(6):1377-1384.
Justino, M.C. et al. (Apr. 6, 2007). "*Escherichia coli* Di-iron YtfE Protein is Necessary for the Repair of Stress-damaged Iron-Sulfur Clusters," *The Journal of Biological Chemistry* 282(14):10352-10359.
Justino, M.C. et al. (2009) "Di-iron Proteins of the Ric Family are Involved in Iron-sulfur Cluster Repair," *Biometals* 22:99-108.
Kajiwara, S. et al. (1997). "Expression of an Exogenous Isopentenyl Diphosphate Isomerase Gene Enhances Isoprenoid Biosynthesis in *Escherichia coli*," *Biochem. J.* 324:421-426.
Kajiwara, Y. et al. (1997). "Production of Acid-Stable α-Amylase by *Aspergillus kawachii* During Barley *Shochu-Koji* Production," *Journal of Fermentation and Bioengineering* 84(3):224-227.
Kakuda, H. et al. (Jun. 13, 1994). "Identification and Characterization of the *ackA* (Acetate Kinase A)-*pta* (Phosphotransacetylase) Operon and Complementation Analysis of Acetate Utilization by an *ackA-pta* Deletion Mutant of *Escherichia coli*," *J. Biochem.* 116:916-922.
Kelley, J.M. et al. (1985). "Transformation of *Aspergillus niger* by the *amdS* Gene of *Aspergillus nidulans*," *The EMBO Journal* 4(2):475-479.

(56) References Cited

OTHER PUBLICATIONS

Kimchi-Sarfaty, C. et al. (Jan. 26, 2007). "A 'Silent' Polymorphism in the *MDR1* Gene Changes Substrate Specificity," *Science* 315:525-528.

Kisselev, L. (Jan. 2002). "Polypeptide Release Factors in Prokaryotes and Eukaryotes: Same Function, Different Structure," *Structure* 10:8-9.

Koppisch, A.T. et al. (2002). "*E. coli* MEP Synthase: Steady-State Kinetic Analysis and Substrate Binding," *Biochemistry* 41:236-243.

Kovach, M.E. et al. (1995). "Four New Derivatives of the Broad-Host-Range Cloning Vector pBBR1MCS, Carrying Different Antibiotic-Resistance Cassettes," *Gene* 166:175-176.

Leonardi, R. et al. (2003, e-pub. Mar. 5, 2003). "Thiamine Biosynthesis in *Escherichia coli*: Isolation and Initial Characterisation of the ThiGH Complex," *FEBS Letters* 539(1-3):95-99.

Leonardi, R. et al. (Apr. 23, 2004). "Thiamine Biosynthesis in *Escherichia coli*. In Vitro Reconstitution of the Thiazole Synthase Activity," *J. Biol. Chem.* 279(17):17054-17062.

Lerner, C.G. et al. (1990). "Low Copy Number Plasmids for Regulated Low-Level Expression of Cloned Genes in *Escherichia coli* with Blue/White Insert Screening Capability," *Nucleic Acids Research* 18(15):4631.

Lindberg, P. et al. (Jan. 2010). "Engineering a Platform for Photosynthetic Isoprene Production in Cyanobacteria, Using *Synechocystis* as the Model Organism," *Metabolic Engineering* 12(1):70-79.

Loiseau, L. et al. (Aug. 21, 2007). "ErpA, an Iron-Sulfur (Fe-S) Protein of the A-type Essential for Respiratory Metabolism in *Escherichia coli*," *PNAS* 104(34):13626-13631.

Lüttgen, H. et al. (Feb. 1, 2000). "Biosynthesis of Terpenoids: YchB Protein of *Escherichia coli* Phosphorylates the 2-hydroxy Group of 4-diphosphocytidyl-2C-methyl-D-erythritol," *PNAS* 97(3):1062-1067.

Lynch, M.D. et al. (Jan. 2007). "SCALEs: Multiscale Analysis of Library Enrichment," *Nature Methods* 4(1):87-93.

Martin, V. et al. (Jul. 2003). "Engineering a Mevalonate Pathway in *Escherichia coli* for Production of Terpenoids," *Nature Biotechnology* 21(7):796-802.

Maurus, R. et al. (2003). "Insights into the Evolution of Allosteric Properties. The NADH Binding Site of Hexameric Type II Citrate Synthases," *Biochemistry* 42:5555-5565.

Miller, B. et al. (Jul. 2001, e-pub. May 10, 2001). "First Isolation of an Isoprene Synthase Gene from Poplar and Successful Expression of the Gene in *Escherichia coli*," *Planta*. 213(3):483-487.

Nackley, A.G. et al. (Dec. 22, 2006). "Human Caechol-*O*-Methyltransferase Haplotypes Modulate Protein Expression by Altering mRNA Secondary Structure," *Science* 314:1930-1933.

NCBI. (2012). Located at <http://www.ncbi.nlm.nih.gov/> last visited on May 29, 2012, two pages.

Nemeria, N. et al. (Jun. 3, 2005). "Glutamate 636 of the *Escherichia coli* Pyruvate Dehydrogenase-E1 Participates in Active Center Communication and Behaves as an Engineered Acetolactate Synthase With Unusual Stereoselectivity," *J. Biol. Chem.* 280(22):21473-21482.

Ner, S.S. et al. (Nov. 8, 1983). "Complete Sequence of the *glt* A Gene Encoding Citrate Synthase in *Escherichia coli*," *Biochemistry* 22(23):5243-5249.

Nevalainen, K.M.H. et al. (1992). "The Molecular Biology of *Trichoderma* and Its Application to the Expression of Both Homologous and Heterologous Genes," Chapter 6 in *Molecular Industrial Mycology, Systems and Applications for Filamentous Fungi*, Leong, S.A. et al. eds., Marcel Dekker Inc.: New York, NY, pp. 129-148.

Nunberg, J.H. et al. (Nov. 1984). "Molecular Cloning and Characterization of the Glucoamylase Gene of *Aspergillus awamori*," *Mol. Cell. Biol.* 4(11):2306-2315.

Ogasawara, H. et al. (Aug. 2007). "PdhR (Pyruvate Dehydrogenase Complex Regulator) Controls the Respiratory Electron Transport System in *Escherichia coli*," *Journal of Bacteriology* 189(15):5534-5541.

Oh, M-K. et al. (Apr. 12, 2002). "Global Expression Profiling of Acetate-grown *Escherichia coli*," *J. Biol. Chem.* 277(15):13175-13183.

Okada, K. et al. (May 27, 2005). "Cyanobacterial Non-mevalonate Pathway. (E)-4-Hydroxy-3-Methylbut-2-Enyl Diphosphate Synthase Interacts with Ferredoxin in *Thermosynechococcus elongatus* BP-1," *J. Biol. Chem.* 280(21):20672-20679.

Oulmouden, A. et al. (1991). "Nucleotide Sequence of the *ERG12* Gene of *Saccharomyces cerevisiae* Encoding Mevalonate Kinase," *Curr. Genet.* 19:9-14.

Palmeros, B. et al. (2000). "A Family of Removable Cassettes Designed to Obtain Antibiotic-Resistance-Free Genomic Modifications of *Escherichia coli* and Other Bacteria," *Gene* 247(1-2):255-264.

Penttila, M. et al. (1987). "A Versatile Transformation System for the Cellulolytic Filamentous Fungus *Trichoderma reesei*," *Gene* 61:155-164.

Perrenoud, A. et al. (May 2005). "Impact of Global Transcriptional Regulation by ArcA, ArcB, Cra, Crp, Cya, Fnr, and Mlc on Glucose Catabolism in *Escherichia coli*," *Journal of Bacteriology* 187(9):3171-3179.

Pourquié, J. et al. (1988). "Scale Up of Cellulase Production and Utilization," in *Biochemistry and Genetics of Cellulose Degradation*, Aubert, J-P. et al. eds., Academic Press: San Diego, CA, pp. 71-86.

Puan, K-J. et al. (2005). "*fldA* is an Essential Gene Required in the 2-*C*-methyl-D-erythritol 4-phosphate Pathway for Isoprenoid Biosynthesis," *FEBS Letters* 579:3802-3806.

Rohdich, F. et al. (Oct. 12, 1999). "Cytidine 5'-triphosphate-dependent Biosynthesis of Isoprenoids: YgbP Protein of *Escherichia coli* Catalyzes the Formation of 4-Diphosphocytidyl-2-*C*-methylerythritol," *PNAS* 96(21):11758-11763.

Rohdich, F. et al. (Jun. 6, 2000). "Biosynthesis of Terpenoids: 4-Diphosphocytidyl-2C-methyl-D-erythritol Synthase of *Arabidopsis thaliana*," *PNAS* 97(12):6451-6456.

Romanos, M.A. et al. (Jun. 1992). "Foreign Gene Expression in Yeast: a Review," *Yeast* 8(6):423-488.

Sakamoto, I, et al. (2000), "Synthesis of 2-*C*-Methyl-D-erythritol and 2-*C*-Methyl-L-threitol; Determination of the Absolute Configuration of 2-*C*-Methyl-1,2,3,4-butanetetrol Isolated from *Phlox sublata L*," *Biosci. Biotechnol. Biochem.* 64(9):1915-1922.

Sánchez, A.M. et al. (May 2005). "Novel Pathway Engineering Design of the Anaerobic Central Metabolic Pathway in *Escherichia coli* to Increase Succinate Yield and Productivity," *Metabolic Engineering* 7(3):229-239.

Sangari, F.J. et al. (Aug. 10, 2010). "A New Family of Enzymes Catalyzing the First Committed Step of the Methylerythritol 4-phosphate (MEP) Pathway for Isoprenoid Biosynthesis in Bacteria," *PNAS* 107(32):14081-14086.

Sasaki, K. et al. (2005, e-pub. Apr. 7, 2005). "Gene Expression and Characterization of Isoprene Synthase from *Populus alba*," *FEBS Letters* 579(11):2514-2518.

Sauna, Z.E. et al. (2007, e-pub. Oct. 17, 2007). "Silent Polymorphisms Speak: How They Affect Pharmacogenomics and the Treatment of Cancer," *Cancer Res.* 67(20):9609-9612.

Sauret-Güeto, S. et al. (2006, e-pub. Jan. 9, 2006). "A Mutant Pyruvate Dehydrogenase E1 Subunit Allows Survival of *Escherichia coli* Strains Defective in 1-deoxy-D-xylulose 5-phosphate Synthase," *FEBS Letters* 580:736-740.

Schnitzler, J-P. et al. (2005, e-pub. Jul. 29, 2005). "Biochemical Properties of Isoprene Synthase in Poplar (*Populus x canescens*)," *Planta* 222(5):777-786.

Schwartz. C.J. et al. (Dec. 18, 2001). "IscR, an Fe-S Cluster-Containing Transcription Factor, Represses Expression of *Escherichia coli* Genes Encoding Fe-S Cluster Assembly Proteins," *PNAS*, 98(26):14895-14900.

Seemann, M. et al. (Nov. 15, 2002). "Isoprenoid Biosynthesis Through the Methylerythritol Phosphate Pathway: The (*E*)-4-Hydroxy-3-methylbut-2-enyl Diphosphate Synthase (GcpE) is a [4Fe-4S] Protein," *Angew. Chem, Int. Ed.* 41(22):4337-4339.

Seemann, M. et al. (2006, e-pub. Feb. 2, 2006). "Isoprenoid Biosynthesis in Plant Chloroplasts Via The MEP Pathway: Direct Thylakoid/Ferredoxin-Dependent Photoreduction of GcpE/IspG," *FEBS Letters* 580(6):1547-1552.

(56) References Cited

OTHER PUBLICATIONS

Seffernick, J.L. et al. (Apr. 2001). "Melamine Deaminase and Atrazine Chlorohydrolase: 98 Percent Identical but Functionally Different," *J. Bacteriol.* 183(8):2405-2410.

Sen, S. et al. (2007). "Developments in Directed Evolution for Improving Enzyme Functions," *Appl. Biochem. Biotechnol.* 143:212-223.

Seta, F.D. et al. (Aug. 1997). "Characterization of *Escherichia coli* Strains With *gapA* and *gapB* Genes Deleted," *Journal of Bacteriology*, 179(16):5218-5221.

Sharkey, T.D. et al. (Feb. 2005). "Evolution of the Isoprene Biosynthetic Pathway in Kudzu," *Plant Physiology* 137:700-712.

Sheir-Neiss, G. et al. (Jul. 1984). "Characterization of the Secreted Cellulases of *Trichoderma reesei* Wild Type and Mutants During Controlled Fermentations," *Appl. Microbiol. Biotechno.* 20(1):46-53.

Shimizu, M. et al. (1969) "Phosphotransacetylase of *Escherichia coli* B, Purification and Properties," *Biochim. Biophys. Acta.* 191(3):550-558.

Silver, G.M. et al. (1991). "Enzymatic Synthesis of Isoprene from Dimethylallyl Diphosphate in Aspen Leaf Extracts," *Plant Physiol.* 97:1588-1591.

Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.

Sivy, T.L. et al. (May 31, 2002). "Isoprene Synthase Activity Parallels Fluctuations of Isoprene Release During Growth of *Bacillus subtilis*," *Biochem. Biophys. Res. Commun.* 294(1):71-75.

Sprenger, G.A. et al. (Nov. 1997). "Identification of a Thiamin-Dependent Synthase in *Escherichia coli* Required for the Formation of the 1-deoxy-D-xylulose 5-phosphate Precursor to Isoprenoids, Thiamin, and Pyridoxol," *PNAS* 94:12857-12862.

Stokell, D.J. et al. (Sep. 12, 2003). "Probing the Roles of Key Residues in the Unique Regulatory NADH Binding Site of Type II Citrate Synthase of *Escherichia coli*," *J. Biol. Chem.* 278(37):35435-35443.

Sulter, G.J. et al. (1990). "Proliferation and Metabolic Significance of Peroxisomes in *Candida boidinii* During Growth on $_D$-alanine or Oleic Acid as the Sole Carbon Source," *Arch. Microbiol.* 153:485-489.

Sutherlin, A. et al. (Aug. 2002). "*Enterococcus faecalis* 3-Hydroxy-3-Methylglutaryl Coenzyme A Synthase, an Enzyme of Isopentenyl Diphosphate Biosynthesis," *J. Bacteriol.* 184(15):4065-4070.

Swiss Institute of Bioinformatics (2012). "ExPASy Bioinformatics Resource Portal," located at <http://expasy.org>, last visited on Dec. 27, 2012, 1 page.

Tchieu, J.H. et al. (Jul. 2001). "The Complete Phosphotransferase System in *Escherichia coli*," *J. Mol. Microbiol. Biotechnol.* 3(3):329-346.

Teymouri, F. et al. (2005, e-pub. Feb. 24, 2005). "Optimization of the Ammonia Fiber Explosion (AFEX) Treatment Parameters for Enzymatic Hydrolysis of Corn Stover," *Bioresource Technology* 96:2014-2018.

Thomason, L.C. et al. (Dec. 2004). "Identification of the *Escherichia coli* K-12 *ybhE* Gene as *pgl*, Encoding 6-Phosphogluconolactonase," *Journal of Bacteriology*, 186(24):8248-8253.

Tokumoto, U. et al. (2001). "Genetic Analysis of the *isc* Operon in *Escherichia coli* Involved in the Biogenesis of Cellular Iron-Sulfur Proteins," *J Biochem.* 130(1):63-71.

Tsay, Y.H. et al. (Feb. 1991). "Cloning and Characterization of *ERG8*, an Essential Gene of *Saccharomyces cerevisiae* That Encodes Phosphomevalonate Kinase," *Mol. Cell. Biol.* 11(2):620-631.

U.S. Appl. No. 13/283,564, filed Oct. 27, 2011 by Beck et al.

Underwood, S.A. et al. (Mar. 2002). "Flux through Citrate Synthase Limits the Growth of Ethanologenic *Escherichia coli* KO11 during Xylose Fermentation," *Applied and Environmental Microbiology* 68(3):1071-1081.

Van Den Hondel, C.A.M.J.J. et al. (1991). "Heterologous Gene Expression in Filamentous Fungi," Chapter 18 in *More Gene Manipulations in Fungi*, Bennet, J.W. et al. eds., Academic Press, Inc.: San Diego, CA, pp. 396-428.

Vander Horn, P.B. et al. (Feb. 1993). "Structural Genes for Thiamine Biosynthetic Enzymes (*thiCEFGH*) in *Escherichia coli* K-12," *J. Bacteriol.* 175(4):982-992.

Vinella, D. et al. (May 29, 2009). "Iron-Sulfur (Fe/S) Protein Biogenesis: Phylogenomic and Genetic Studies of A-Type Carriers," *PLOS Genetics* 5(5):1-16 of e1000497.

Wagner, W.P. et al. (Jan. 2000). "Isoprene Biosynthesis in *Bacillus subtilis* via the Methylerythritol Phosphate Pathway," *J. Nat. Prod.* 63(1):37-40.

Ward, M. et al. (Aug. 1993). "Use of *Aspergillus* Overproducing Mutants, Cured for Integrated Plasmid, to Overproduce Heterologous Proteins," *Appl. Microbiol. Biotechnol.* 39(6):738-743.

Whisstock, J.C. et al. (2003). "Prediction of Protein Function from Protein Sequence and Structure," *Quarterly Reviews of Biophysics* 36(3):307-340.

Wiegand, G. et al. (1986). "Citrate Synthase: Structure, Control, and Mechanism," *Ann. Rev. Biophys. Biophys. Chem.* 15:97-117.

Wishart, M.J. et al. (Nov. 10, 1995). "A Single Mutation Converts a Novel Phosphotyrosine Binding Domain into a Dual-Specificity Phosphatase," *J. Biol. Chem.* 270(45):26782-26785.

Withers, S.T. et al. (Oct. 2007). "Identification of Isopentenol Biosynthetic Genes from *Bacillus subtilis* by a Screening Method Based on Isoprenoid Precursor Toxicity," *Applied and Environmental Microbiology* 73(19):6277-6283.

Witkowski, A. et al. (1999). "Conversion of β-Ketoacyl Synthase to a Malonyl Decarboxylase by Replacement of the Active-Site Cysteine with Glutamine," *Biochemistry* 38:11643-11650.

Wolfe, A. (Mar. 2005). "The Acetate Switch," *Microbiology and Molecular Biology Reviews* 69(1):12-50.

Wolff, M. et al. (2003). "Isoprenoid Biosynthesis Via the Methylerythritol Phosphate Pathway: The ($E$)-4-hydroxy-3-methylbut-2-enyl Diphosphate Reductase (LytB/IspH) from *Escherichia coli* is a [4Fe-4S] Protein," *FEBS Letters* 541:115-120.

Yamada, K. et al. (1989). "Production of Glycerol from Methanol by a Mutant Strain of *Candida boidinii* No. 2201," *Agric. Biol. Chem.* 53(2):541-543.

Yelton, M.M. et al. (Mar. 1984). "Transformation of *Aspergillus nidulans* by Using a *trpC* Plasmid," *PNAS* 81:1470-1474.

Zepeck, F. et al. (Nov. 11, 2005). "Biosynthesis of Isoprenoids. Purification and Properties of IspG Protein from *Escherichia coli*," *J. Org. Chem.* 70(23):9168-9174.

Miller, B. (2001). "Erstmalige Isolierung eines Isoprensynthase-Gens and heterologe Expression des aus der Pappel stammenden Gens sowie Charakterisierung der Eingangsgene des Mevalonat-unabhängigen Isoprenoidbiosyntheseweges aus dem Cyanobakterium Synechococcus Ieopoliensis," located at <http://kups.ub.uni-koeln.de/volltexte/2003/883/pdf/millerbarbara.pdf>, last visited on Feb. 25, 2013, two pages (with English Translation).

\* cited by examiner

BIOLOGICAL PRODUCTION OF PENTOSE SUGARS USING RECOMBINANT CELLS

CROSS-REFERENCE TO RELATED APPLICATIONS

This application claims priority benefit of U.S. provisional patent application No. 61/426,483, filed on Dec. 22, 2010, the content of which is hereby incorporated by reference herein in its entirety.

FIELD OF THE INVENTION

The present invention relates generally to the biological production of pentose sugars, such as 2-methylerythritol (2-ME), 1-deoxyxylulose (1-DX), and monoacetylated-2-C-methylerythritols, using recombinant cells.

BACKGROUND OF THE INVENTION

Production of biochemicals from renewable resources is of strategic interest as society seeks to move to sustainable industrial processes. Fermentation using engineered microorganisms allows the direct conversion of a range of carbon-sources (sugars, lipids etc.) to compounds of greater value under mild conditions, such as pentose sugars.

Pentose sugars are found in a number of industries, for example as food additives/preservatives, sweeteners, in cosmetic formulations, as chiral precursors for pharmaceuticals and as building blocks for detergents and other chemicals. There exists a need for more commercially efficient ways of producing pentose sugars in a sustainable manner. The invention described herein addresses this need and provides additional benefits as well.

All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention.

BRIEF SUMMARY OF THE INVENTION

The invention provides, inter alia, compositions and methods for the biological production of pentose sugars, such as 2-methylerythritol (2-ME), 1-deoxyxylulose (1-DX), and monoacetylated-2-C-methylerythritols, using recombinant cells.

Accordingly, in one aspect, the invention provides for methods of producing a pentose sugar by (a) culturing recombinant cells comprising (i) a heterologous nucleic acid encoding a DXS and/or DXR polypeptide and/or (ii) one or more copies of an endogenous nucleic acid encoding a DXS and/or DXR polypeptide, wherein the cells are cultured under conditions suitable for producing a pentose sugar and (b) producing said pentose sugar. In one aspect, the recombinant cells further comprise (iii) a heterologous nucleic acid encoding a phosphatase and/or (ii) one or more copies of an endogenous nucleic acid encoding a phosphatase. In another aspect, the pentose sugar is selected from the group consisting of 2-methylerythritol (2-ME) and 1-deoxyxylulose (1-DX). In another aspect, the pentose sugar is 2-methylerythritol (2-ME). In another aspect, the recombinant cells are capable of producing a cumulative titer of 2-ME of at least about 20 g/L. In another aspect, the recombinant cells are capable of producing a cumulative titer of 2-ME of at least about 30 g/L. In another aspect, the recombinant cells are capable of producing a cumulative titer of 2-ME of at least about 45 g/L.

In another aspect, the invention provides for methods of producing 2-methylerythritol (2-ME), the method comprising: (a) culturing recombinant cells comprising (i) a heterologous nucleic acid encoding a DXS and/or DXR polypeptide and/or (ii) one or more copies of an endogenous nucleic acid encoding a DXS and/or DXR polypeptide, wherein the cells are cultured under conditions suitable for producing 2-ME and (b) producing 2-ME. In one aspect, the cells are capable of producing at least about 45 g/L of 2-ME.

In another aspect, the invention provides for methods of producing 2-methylerythritol (2-ME), the method comprising: (a) culturing recombinant cells comprising (i) a heterologous nucleic acid encoding a DXS and/or DXR polypeptide and/or (ii) one or more copies of an endogenous nucleic acid encoding a DXS and/or DXR polypeptide and/or (iii) a heterologous nucleic acid encoding a phosphatase and/or (ii) one or more copies of an endogenous nucleic acid encoding a phosphatase, wherein the cells are cultured under conditions suitable for producing 2-ME and (b) producing 2-ME. In one aspect, the cells are capable of producing at least about 45 g/L of 2-ME.

In another aspect, the invention provides for methods for producing at least one pentose sugar, the method comprising: (a) culturing recombinant cells described herein under conditions suitable for producing a pentose sugar and (b) producing the pentose sugar, wherein the pentose sugar is selected from the group consisting of 2-methylerythritol (2-ME), 1-deoxyxylulose (1-DX), and monoacetylated-2-C-methylerythritol. In one aspect, the cells are capable of producing at least about 45 g/L of 2-ME. In other aspects, any of the methods for production also include recovering the pentose sugar.

In other aspects, the invention provides for recombinant cells capable of producing a pentose sugar, the cell comprising (a) culturing recombinant cells comprising (i) a heterologous nucleic acid encoding a DXS and/or DXR polypeptide and/or (ii) one or more copies of an endogenous nucleic acid encoding a DXS and/or DXR polypeptide and optionally (iii) a heterologous nucleic acid encoding a phosphatase and/or (ii) one or more copies of an endogenous nucleic acid encoding a phosphatase. In one aspect, the cells are capable of producing at least about 45 g/L of 2-ME.

In any of the aspects above, the recombinant cells can also include one or more heterologous nucleic acids encoding a DXP pathway polypeptide (other than a DXS and/or DXR polypeptide) and/or (ii) one or more copies of an endogenous nucleic acid encoding a DXP pathway polypeptide (other than a DXS and/or DXR polypeptide).

In any of the aspects herein, the recombinant cells can be bacterial, algal, fungal or yeast cells. In one aspect, the cells are bacterial cells. In another aspect, the bacterial cells are gram-positive bacterial cells or gram-negative bacterial cells. In another aspect, the bacterial cells are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells. In another aspect, the recombinant cells can be a bacterial cell. In any of the aspects above, the recombinant cells can be *E. coli*.

In any of the aspects above, the DXP pathway polypeptide can be IspG. In some aspects, only one IspG is used. In other aspects, two types of IspG are used. In another aspect, the IspG polypeptides are from *T. elongatus* or *E. coli*. In another aspect, the DXP pathway enzyme is selected from the group of DXS, DXR, MCT, CMK, MCS, HDR (IspH), and IDI. In another aspect, the additional DXP pathway enzyme is selected from the group of DXS, DXR, HDR (IspH), and IDI.

In any of the aspects above, the recombinant cells can also include an iron-sulfur cluster-interacting redox polypeptide. Such iron-sulfur cluster-interacting redox polypeptides can be ferredoxins and flavodoxins.

In any of the aspects above, the recombinant cells can also include a heterologous nucleic acid encoding for PGL polypeptide or one or more copies of endogenous nucleic acid encoding for PGL polypeptide. In any of the aspects above, the PGL nucleic acid is integrated into the host cell's chromosome.

In any of the aspects above, the recombinant cells can also include one or more heterologous nucleic acid encoding an isopentenyl-diphosphate delta-isomerase (IDI) polypeptide or one or more copies of an endogenous nucleic acid encoding an IDI polypeptide.

In another aspect, the invention provides for a cell culture comprising the recombinant cell as described herein. In one aspect, the cell culture produces at least about 45 g/L of 2-ME.

In another aspect, the invention also provides for systems for making pentose sugars, such as 2-methylerythritol (2-ME), 1-deoxyxylulose (1-DX), and monoacetylated-2-C-methylerythritols, using recombinant cells as described herein.

BRIEF DESCRIPTION OF THE DRAWINGS

FIG. 1 also depicts how 1-deoxy-D-xylulose (or 1-DX) and 2-C-Methyl-D-erythritol (or 2-ME) can be obtained the removal of the phospatate group by phosphatase.

DETAILED DESCRIPTION OF THE INVENTION

Figure 1:
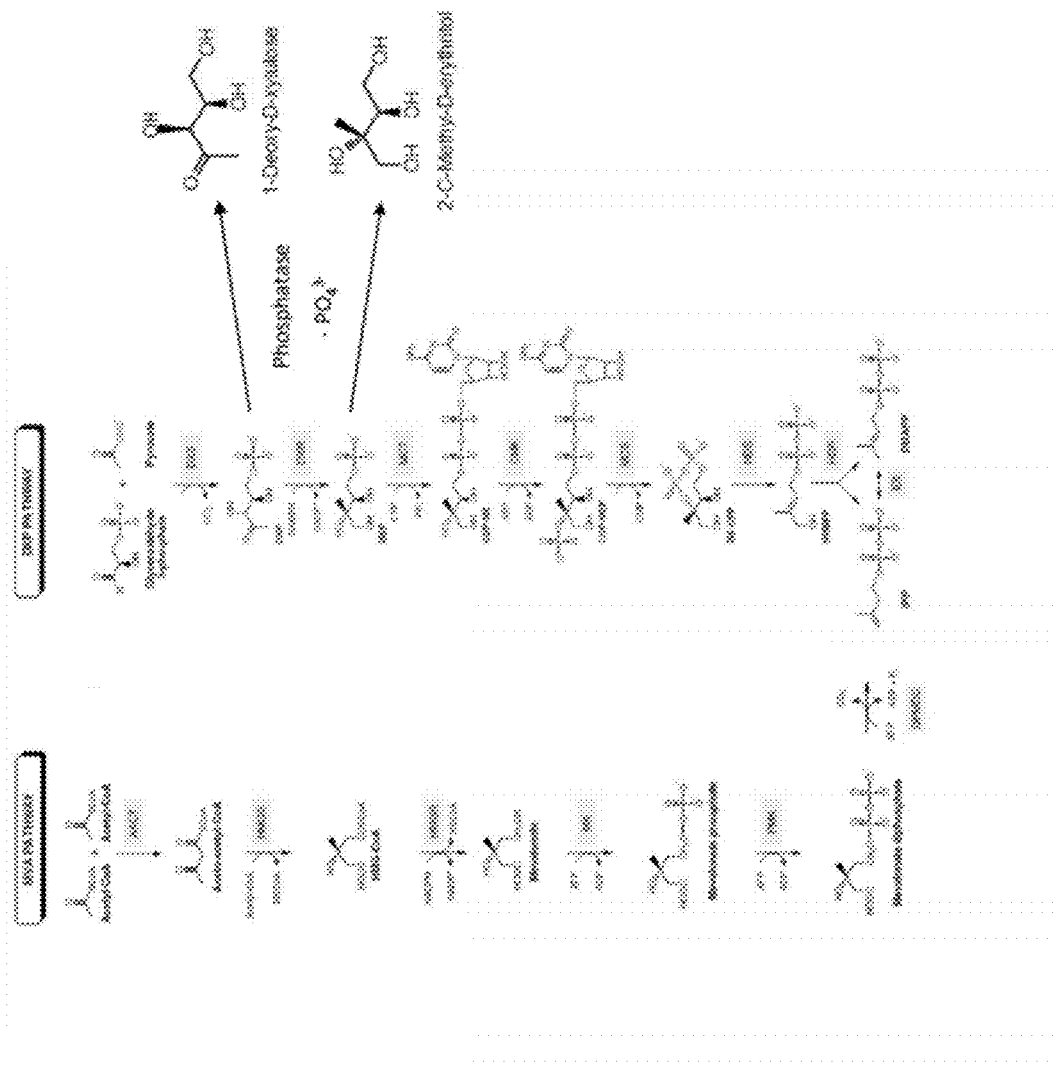
FIG. 1 shows MVA and DXP metabolic pathways for isoprene (based on F. Bouvier et al., Progress in Lipid Res. 44:357-429, 2005). The following description includes alternative names for each polypeptide in the pathways and a reference that discloses an assay for measuring the activity of the indicated polypeptide (each of these references are each hereby incorporated herein by reference in their entireties). Mevalonate Pathway: AACT; Acetyl-CoA acetyltransferase, MvaE, EC 2.3.1.9. Assay: J. Bacteriol. 184:2116-2122, 2002; HMGS; Hydroxymethylglutaryl-CoA synthase, MvaS, EC 2.3.3.10. Assay: J. Bacteriol. 184:4065-4070, 2002; HMGR; 3-Hydroxy-3-methylglutaryl-CoA reductase, MvaE, EC 1.1.1.34. Assay: J. Bacteriol. 184:2116-2122, 2002; MVK; Mevalonate kinase, ERG12, EC 2.7.1.36. Assay: Curr Genet. 19:9-14, 1991. PMK; Phosphomevalonate kinase, ERG8, EC 2.7.4.2, Assay: Mol. Cell. Biol. 11:620-631, 1991; DPMDC; Diphosphomevalonate decarboxylase, MVD1, EC 4.1.1.33. Assay: Biochemistry 33:13355-13362, 1994; IDI; Isopentenyl-diphosphate delta-isomerase, IDI1, EC 5.3.3.2. Assay: J. Biol. Chem. 264:19169-19175, 1989. DXP Pathway: DXS; 1-Deoxyxylulose-5-phosphate synthase, dxs, EC 2.2.1.7. Assay: PNAS 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay: PNAS 97: 6451-6456, 2000; CMK; 4-Diphosphocytidyl-2-C-methyl-D-erythritol kinase, IspE, EC 2.7.1.148. Assay: PNAS 97:1062-1067, 2000; MCS; 2C-Methyl-D-erythritol 2,4-cyclodiphosphate synthase, IspF, EC 4.6.1.12. Assay:PNAS 96:11758-11763, 1999; HDS; 1-Hydroxy-2-methyl-2-(E)-butenyl 4-diphosphate synthase, ispG, EC 1.17.4.3. Assay: J. Org. Chem. 70:9168-9174, 2005; HDR; 1-Hydroxy-2-methyl-2-(E)-butenyl 4-diphosphate reductase, IspH, EC 1.17.1.2. Assay:JACS 126:12847-12855, 2004.

The invention provides, inter alia, systems, compositions and methods for the biological production of pentose sugars, such as 2-methylerythritol (2-ME), 1-deoxyxylulose (1-DX), and monoacetylated-2-C-methylerythritols, using recombinant cells. As further detailed herein, the inventors have observed that engineered microorganisms (e.g., *E. coli* BL21 strain) are capable of producing significant amounts of the pentose (five-carbon) sugars, such as 2-C-methyl-D-erythritol or 2-methylerythritol (2-ME) and 1-deoxy-D-xylulose (1-DX). The production of these pentose sugars can be achieved as part of a process for the conversion of glucose to isoprene (2-methyl-1,3-butadiene) via the deoxyxylulose phosphate (DXP) pathway. These pentose sugars have utility in a number of industries, for example as food additives/preservatives, sweeteners, in cosmetic formulations, as chiral precursors for pharmaceuticals and as building blocks for detergents and other chemicals.

DEFINITIONS

Unless defined otherwise, the meanings of all technical and scientific terms used herein are those commonly understood by one of skill in the art to which this invention belongs. Singleton, et al., Dictionary of Microbiology and Molecular Biology, 2nd ed., John Wiley and Sons, New York (1994), and Hale & Marham, The Harper Collins Dictionary of Biology, Harper Perennial, N.Y. (1991) provide one of skill with a general dictionary of many of the terms used in this invention. It is to be understood that this invention is not limited to the particular methodology, protocols, and reagents described, as these may vary. One of skill in the art will also appreciate that any methods and materials similar or equivalent to those described herein can also be used to practice or test the invention. The headings provided herein are not limitations of the various aspects or aspects of the invention which can be had by reference to the specification as a whole.

As used herein, the term "polypeptides" includes polypeptides, proteins, peptides, fragments of polypeptides, and fusion polypeptides.

As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide. An isolated polypeptide can be a non-naturally occurring polypeptide.

By "heterologous polypeptide" is meant a polypeptide encoded by a nucleic acid sequence derived from a different organism, species, or strain than the host cell. In some aspects, a heterologous polypeptide is not identical to a wild-type polypeptide that is found in the same host cell in nature.

As used herein, a "nucleic acid" refers to two or more deoxyribonucleotides and/or ribonucleotides covalently joined together in either single or double-stranded form.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. In some cases, a recombinant nucleic acid is a nucleic acid that encodes a non-naturally occurring polypeptide.

By "heterologous nucleic acid" is meant a nucleic acid sequence derived from a different organism, species or strain than the host cell. In some aspects, the heterologous nucleic acid is not identical to a wild-type nucleic acid that is found in the same host cell in nature.

As used herein, the phrase, "various genes and polypeptides associated with the DXP pathway," or "DXP pathway associated nucleic acid(s) or polypeptide(s)" refers to any nucleic acid or polypeptide that interacts with DXP pathway polypeptides or nucleic acids, including, but not limited to, a terpene synthase (e.g., ocimene synthase, farnesene synthase, and artemesinin synthase), either directly or indirectly.

For use herein, unless clearly indicated otherwise, use of the terms "a", "an," and the like refers to one or more.

Reference to "about" a value or parameter herein includes (and describes) aspects that are directed to that value or parameter per se. For example, description referring to "about X" includes description of "X." Numeric ranges are inclusive of the numbers defining the range.

It is understood that aspects and aspects of the invention described herein include "comprising," "consisting," and "consisting essentially of" aspects and aspects.

Compositions and Methods Involving Recombinant Cells Capable of Producing Pentose Sugars As described in greater detail and further exemplified herein, the inventions provides for compositions and methods for the biological production of pentose sugars using recombinant cells. Pentose sugars that can be made include, but are not limited to, 2-methylerythritol (2-ME), 1-deoxyxylulose (1-DX), and monoacetylated-2-C-methylerythritols. In one aspect, the invention provides for compositions of and methods for producing pentose sugars using recombinant cells that contain (i) a heterologous nucleic acid encoding a DXS and/or DXR polypeptide and/or (ii) one or more copies of an endogenous nucleic acid encoding a DXS and/or DXR polypeptide and optionally (iii) a heterologous nucleic acid encoding a phosphatase and/or (ii) one or more copies of an endogenous nucleic acid encoding a phosphatase.

Some recombinant cells (e.g., BL21 *E. coli* strain) have been engineered to utilize the DXP pathway for making isoprene, however, the inventors have observed that the production of pentose sugars (such as 2-ME) is decreased when isoprene production is increased. Thus, for commercial production of pentose sugars, it is recommended that the system be engineered as to decrease the amount of isoprene production so that more pentose sugars, such as 2-ME, can be made.

A non-limiting way of accomplishing this is to not introduce heterologous nucleic acids encoding for isoprene synthase or additional copies of endogenous isoprene synthase into the host cell. In one aspect, a recombinant cell is made such that it contains one or more of the DXP pathway polypeptides, such as IspG, and does not include a heterologous nucleic acid encoding for isoprene synthase or additional copies of endogenous isoprene synthase.

As shown in FIG. 1, 1-deoxy-D-xylulose (1-DX) can be made by the removal of a phosphate group from the DXP. Accordingly, the production of 1-DX can be achieved by overexpressing the DXS enzyme. This overexpression can be achieved by the introduction of a heterologous nucleic acid encoding a DXS polypeptide and/or (ii) one or more copies of an endogenous nucleic acid encoding a DXS polypeptide. For increasing production of 1-DX as a end product, one of skill in the art can increase 1-DX by increasing the amount of DXP along with increasing the amount of phosphatase in the system. This can be achieved by the introduction of a heterologous nucleic acid encoding a phosphatase and/or (ii) one or more copies of an endogenous nucleic acid encoding a phosphatase.

As shown in FIG. 1, 2-C-methyl-D-erythritol (2-ME) can be made by the removal of a phosphate group from the MEP compound. The production of 2-ME can be achieved by overexpressing the DXR enzyme. This overexpression can be achieved by the introduction of a heterologous nucleic acid encoding a DXR polypeptide and/or (ii) one or more copies of an endogenous nucleic acid encoding a DXR polypeptide. For increasing production of 2-ME as a end product, one of skill in the art can increase 2-ME by increasing the amount of DXP along with increasing the amount of phosphatase in the system. This can be achieved by the introduction of a heterologous nucleic acid encoding a phosphatase and/or (ii) one or more copies of an endogenous nucleic acid encoding a phosphatase.

In some cases, production of both 1-DX and 2-ME is desired. In that case, the overexpression of both DXS and DXR enzymes should be used. Production of both 1-DX and 2-ME can be achieved by using recombinant cells that contain (i) a heterologous nucleic acid encoding a DXS and/or DXR polypeptide and/or (ii) one or more copies of an endogenous nucleic acid encoding a DXS and/or DXR polypeptide and optionally (iii) a heterologous nucleic acid encoding a phosphatase and/or (ii) one or more copies of an endogenous nucleic acid encoding a phosphatase. The same would be equally applicable for the production of monoacetylated-2-C-methylerythritols and other pentose sugars.

In some instances, the other DXP pathway enzymes may be overexpressed, in conjunction with the expression or overexpression with DXS and/or DXP, to achieve production of pentose sugars. The DXP pathway enzymes are described in greater detail below. One such DXP enzyme that can be used is IspG or HDS.

IspG Enzymes and Systems

IspG enzymes are part of the lower DXP pathway. IspG genes code for HDS polypeptides, which convert 2-C-methyl-D-erythritol 2,4-cyclodiphoshphate (ME-CPP or cMEPP) into (E)-4-hydroxy-3-methylbut-2-en-1-yl-diphosphate (HMBPP or HDMAPP).

For increasing IspG activity, one option is to express more of the endogenous *E. coli* IspG system. The systems, compositions of recombinant cells, and methods described herein utilize a different approach where IspG activity and subsequent pentose sugar production is enhanced by over-expression of two types of IspG genes. In one aspect, the two types of IspG are *E. coli* and *T. elongatus* IspG system.

The *E. coli* IspG system includes, but is not limited to, the enzyme IspG (encoded by the gene ispG) and the required flavodoxin redox partner FldA (encoded by the gene fldA). The *T. elongatus* IspG system includes, but is not limited to, the enzyme IspG (encoded by the gene gcpE) and the required ferredoxin redox partner Fd (encoded by the petF gene), as well as the nonessential ferredoxin-NADP(+) oxidoreductase redox partner Fpr (encoded by the petH gene). In some instances, Fpr activity is not required for the *T. elongatus* IspG to function within *E. coli* where the activity of the *T. elongatus* IspG was found to be dependent on the Fd cofactor. The fpr gene of *E. coli* is nonessential and the activity of the *T. elongatus* IspG within *E. coli* depends on co-expression of the *T. elongatus* Fd.

Without being bound by theory, the *E. coli* IspG system and the *T. elongatus* IspG system are believed to ultimately obtain the electrons necessary to perform their catalytic function from NADPH via some flavodoxin/ferredoxin-NADP(+) oxidoreductase activity. Enzymes with flavodoxin/ferredoxin-NADP(+) oxidoreductase activity have been demonstrated in vitro to fulfill the role of electron transport to the required flavodoxin and ferredoxin cofactors essential for IspG activity, however the in vivo physiological relevance of these reductases has not been shown and, as such, cannot be predictable.

Exemplary Polypeptides and Nucleic Acids

As noted above, recombinant cells of the invention and their progeny are engineered to have one or more heterologous nucleic acids encoding a DXS and/or DXR polypeptide and/or one or more copies of an endogenous nucleic acid encoding a DXS and/or DXR polypeptide. In one aspect, the recombinant cells can have one IspG enzyme or two types of IspG enzymes and one or more DXP pathway polypeptide(s). In some aspect, the cell can further contain various iron-sulfur cluster-interacting redox polypeptides and nucleic acids, DXP pathway associated polypeptide, MVA pathway polypeptides and nucleic acids, PGL polypeptides and nucleic acids and IDI polypeptides and nucleic acids.

Polypeptides includes polypeptides, proteins, peptides, fragments of polypeptides, and fusion polypeptides. In some aspects, the fusion polypeptide includes part or all of a first polypeptide (e.g., an iron-sulfur cluster-interacting redox polypeptide, DXP pathway polypeptide, DXP pathway associated polypeptide, and IDI polypeptide, or catalytically active fragment thereof) and may optionally include part or all of a second polypeptide (e.g., a peptide that facilitates purification or detection of the fusion polypeptide, such as a His-tag). In some aspects, the fusion polypeptide has an activity of two or more DXP pathway polypeptides.

In particular aspects, the nucleic acid includes a segment of or the entire nucleic acid sequence of any iron-sulfur cluster-interacting redox nucleic acid, IspG, DXP pathway nucleic acid, DXP pathway associated nucleic acid, or IDI nucleic acid. In some aspects, the nucleic acid includes at least or about 50, 100, 150, 200, 300, 400, 500, 600, 700, 800, or more contiguous nucleotides from a iron-sulfur cluster-interacting redox nucleic acid, IspG, DXP pathway nucleic acid, DXP pathway associated nucleic acid, or IDI nucleic acid. In some aspects, the nucleic acid has one or more mutations compared to the sequence of a wild-type (i.e., a sequence occurring in nature) IspG, iron-sulfur cluster-interacting redox nucleic acid, DXP pathway nucleic acid, DXP pathway associated nucleic acid, or IDI nucleic acid. In some aspects, the nucleic acid has one or more mutations (e.g., a silent mutation) that increase the transcription or translation of IspG, iron-sulfur cluster-interacting redox nucleic acid, DXP pathway nucleic acid, DXP pathway associated nucleic acid, or IDI nucleic acid. In some aspects, the nucleic acid is a degenerate variant of any nucleic acid encoding an iron-sulfur cluster-interacting redox polypeptide, DXP pathway polypeptide, DXP pathway associated polypeptide, or IDI polypeptide.

The accession numbers of exemplary DXP pathway polypeptides and nucleic acids are listed in Appendix 1 of WO 2009/076676.

Exemplary Iron-sulfur Cluster-Interacting Redox Polypeptides and Nucleic Acids

Iron-sulfur cluster-interacting redox polypeptide plays an essential role in the DXP pathway for isoprenoid biosynthesis. Exemplary iron-sulfur cluster-interacting redox polypeptides include polypeptides, fragments of polypeptides, peptides, and fusions polypeptides that have at least one activity of a iron-sulfur cluster-interacting redox polypeptide. Standard methods can be used to determine whether a polypeptide has iron-sulfur cluster-interacting redox polypeptide activity by using a hydrogenase-linked assay measuring the rate of metronidazole[1-(2-hydroxyethyl)-2-methyl-5-nitroimidazole] reduction (Chen and Blanchard, Analytical Biochem, 93:216-222 (1979)).

Exemplary iron-sulfur cluster-interacting redox polypeptide nucleic acids include nucleic acids that encode a polypeptide, fragment of a polypeptide, peptide, or fusion polypeptide that has at least one activity of an iron-sulfur cluster-interacting redox polypeptide. Exemplary iron-sulfur cluster-interacting redox polypeptides and nucleic acids include naturally-occurring polypeptides and nucleic acids from any of the source organisms described herein as well as mutant polypeptides and nucleic acids derived from any of the source organisms described herein.

Iron-sulfur cluster-interacting redox polypeptide is a polypeptide that is capable of transferring electrons to a polypeptide containing an iron-sulfur cluster. An iron-sulfur cluster-interacting redox polypeptide includes, but is not limited to, flavodoxin (e.g., flavodoxin I), flavodoxin reductase, ferredoxin (e.g., ferredoxin I), ferredoxin-NADP+ oxidoreductase, and genes or polypeptides encoding thereof (e.g., fpr or fldA). For example, DXP pathway polypeptide HDS (GcpE) is a metallo-enzyme possessing a $[4Fe-4S]^{2+}$ center and catalyzes the reduction of cMEPP into HMBPP via two successive one-electron transfers mediated by the reduction of $[4Fe-4S]^{2+}$ center in the presence of flavodoxin/flavodoxin reductase (see, Wolff et al., *FEBS Letters*, 541:115-120 (2003)). Similarly, DXP pathway polypeptide HDR (LytB) is also a Fe/S protein catalyzing the reduction of HMBPP into IPP or DMAPP via two successive one-electron transfers in the presence of flavodoxin/flavodoxin reductase/NADPH system. See, for example, Seemann, M. et al. *Agnew. Chem. Int. Ed.*, 41: 4337-4339 (2002); Wolff, M. et al., *FEBS Letters*, 541: 115-120 (2003)).

Flavodoxin is a protein that is capable of transferring electrons and contains the prosthetic group flavin mononucleotide. In *Escherichia coli* (*E. coli*), flavodoxin is encoded by the fldA gene and reduced by the FAD-containing protein NADPH:ferredoxin oxidoreductase, and plays an essential role in the DXP pathway for isoprenoid biosynthesis (see, example, Kia-Joo, P. et al. *FEBS Letters*, 579: 3802-3806, 2005).

Ferredoxin is a protein that is capable of transferring electron and contains iron and labile sulfur in equal amounts and plays an essential role in the DXP pathway for isoprenoid biosynthesis. For example, HDS from plants and cyanobacteria have been shown to be ferredoxin, rather than flavodoxin-dependent, enzymes (Seemann et al., *FEBS Lett.*, 580(6):1547-52 (2006)).

Fpr encodes flavodoxin/ferredoxin NADPH-oxidoreductase and provides the necessary electron derived from NADPH via FldA for HDS and HDR to perform their catalytic functions (reviewed in report by L. A. Furgerson, *The Mevalonate-Independent Pathway to Isoprenoid Compounds: Discovery, Elucidation, and Reaction Mechanisms*, published Feb. 13, 2006).

Exemplary DXP Pathway Polypeptides and Nucleic Acids

Exemplary DXP pathways polypeptides include, but are not limited to any of the following polypeptides: DXS polypeptides, DXR polypeptides, MCT polypeptides, CMK polypeptides, MCS polypeptides, HDS polypeptides, HDR polypeptides, IDI polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids derived from any of the source organisms described herein. In some aspects, the heterologous nucleic acid encoding a DXP pathway polypeptide is operably linked to a constitutive promoter. In some aspects, the heterologous nucleic acid encoding an DXP pathway polypeptide is operably linked to a strong promoter.

In particular, DXS polypeptides convert pyruvate and D-glyceraldehyde 3-phosphate into 1-deoxy-d-xylulose 5-phosphate (DXP). Standard methods can be used to determine whether a polypeptide has DXS polypeptide activity by measuring the ability of the polypeptide to convert pyruvate and D-glyceraldehyde 3-phosphate in vitro, in a cell extract, or in vivo.

DXR polypeptides convert 1-deoxy-D-xylulose 5-phosphate (DXP) into 2-C-methyl-D-erythritol 4-phosphate (MEP). Standard methods can be used to determine whether a polypeptide has DXR polypeptides activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptides activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptides activity by measuring the ability of the polypeptide to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2,4-cyclodiphosphate (ME-CPP or cMEPP). Standard methods can be used to determine whether a polypeptide has MCS polypeptides activity by measuring the ability of the polypeptide to convert CDP-MEP in vitro, in a cell extract, or in vivo.

HDS polypeptides convert 2-C-methyl-D-erythritol 2,4-cyclodiphosphate into (E)-4-hydroxy-3-methylbut-2-en-1-yl diphosphate (HMBPP or HDMAPP). Standard methods can be used to determine whether a polypeptide has HDS polypeptides activity by measuring the ability of the polypeptide to convert ME-CPP in vitro, in a cell extract, or in vivo.

HDR polypeptides convert (E)-4-hydroxy-3-methylbut-2-en-1-yl diphosphate into isopentenyl diphosphate (IPP) and dimethylallyl diphosphate (DMAPP). In one embodiment, the ispH gene can be used to encode for HDR polypeptides. IspH is also known as 1-hydroxy-2-methyl-2-(E)-butenyl 4-diphosphate reductase, 4Fe-4S protein, ECK0030, JW0027, lytB, yaaE, and b0029. Standard methods can be used to determine whether a polypeptide has HDR polypeptides activity by measuring the ability of the polypeptide to convert HMBPP in vitro, in a cell extract, or in vivo.

IDI polypeptides convert isopentenyl diphosphate into dimethylallyl diphosphate. Standard methods can be used to determine whether a polypeptide has IDI polypeptides activity by measuring the ability of the polypeptide to convert isopentenyl diphosphate in vitro, in a cell extract, or in vivo.

Exemplary MVA Pathway Polypeptides and Nucleic Acids

In some aspects of the invention, the cells described in any of the compositions or methods described herein can also include a nucleic acid encoding an MVA pathway polypeptide. In some aspects, the MVA pathway polypeptide is an endogenous polypeptide. In some aspects, the MVA pathway polypeptide is an heterologous polypeptide. In some aspects, the cells comprise one or more additional copies of a heterologous nucleic acid encoding an MVA pathway polypeptide. In some aspects, the cells comprise one or more additional copies of an endogenous nucleic acid encoding an MVA pathway polypeptide. In some aspects, the endogenous nucleic acid encoding an MVA pathway polypeptide operably linked to a constitutive promoter. In some aspects, the endogenous nucleic acid encoding an MVA pathway polypeptide operably linked to a constitutive promoter. In some aspects, the endogenous nucleic acid encoding an MVA pathway polypeptide is operably linked to a strong promoter. In a particular aspect, the cells are engineered to over-express the endogenous MVA pathway polypeptide relative to wild-type cells.

In some aspects, the MVA pathway polypeptide is a heterologous polypeptide. In some aspects, the cells comprise more than one copy of a heterologous nucleic acid encoding an MVA pathway polypeptide. In some aspects, the heterologous nucleic acid encoding an MVA pathway polypeptide is operably linked to a constitutive promoter. In some aspects, the heterologous nucleic acid encoding an MVA pathway polypeptide is operably linked to a strong promoter.

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonate decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein. In addition, variants of MVA pathway polypeptide that confer the result of better pentose sugar production can also be used as well.

Types of MVA pathway polypeptides and/or DXP pathway polypeptides which can be used and methods of making microorganisms (e.g., *E. coli*) encoding MVA pathway polypeptides and/or DXP pathway polypeptides are also described in International Patent Application Publication No. WO 2009/076676 and WO 2010/003007.

One of skill in the art can readily select and/or use suitable promoters to optimize the expression of any of the DXP pathway polypeptides (such as DXS, DXR, HDS or IspG), PGL polypeptides and/or MVA pathway polypeptides. Similarly, one of skill in the art can readily select and/or use suitable vectors (or transfer vehicle) to optimize the expression of these polypeptides. In some aspects, the vector contains a selective marker. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell.

In some aspects, the nucleic acid encoding for any of the DXP pathway polypeptides (such as DXS, DXR, HDS or IspG), PGL polypeptides, or MVA pathway polypeptides integrates into a chromosome of the cells without a selective marker. One of skill in the art would appreciate that integration should occur at a location that is not essential to the host organism. For example, in a bacterial cell (e.g., *E. coli* cell), integration into the origin of replication (or any other essential region of the chromosome) would render the bacteria unable to replicate. Thus, care should be taken to avoid integrating into essential locations of the chromosome in the host organism.

Exemplary Source Organisms

DXP pathway nucleic acid, PGL nucleic acid, iron-sulfur cluster-interacting redox nucleic acid, DXP pathway associated nucleic acid, or IDI nucleic acid (and their encoded polypeptides) can be obtained from any organism that naturally contains these nucleic acids. Thus, DXS, DXR, MCT, CMK, MCS, HDS (IspG), or HDR nucleic acids can be obtained, e.g., from any organism that contains the DXP pathway or contains both the MVA and DXP pathways. IDI and PGL nucleic acid nucleic acids can be obtained, e.g., from any organism that contains the MVA pathway, DXP pathway, or both the MVA and DXP pathways.

In some aspects, the nucleic acid sequence of the iron-sulfur cluster-interacting redox nucleic acid, DXP pathway nucleic acid, DXP pathway associated nucleic acid, or IDI nucleic acid is identical to the sequence of a nucleic acid that is produced by any of the following organisms in nature. In some aspects, the amino acid sequence of iron-sulfur cluster-interacting redox polypeptide, DXP pathway polypeptide, DXP pathway associated polypeptide, or IDI polypeptide is identical to the sequence of a polypeptide that is produced by any of the following organisms in nature. In some aspects, the iron-sulfur cluster-interacting redox nucleic acid, DXP pathway nucleic acid, DXP pathway associated nucleic acid, or IDI nucleic acid or its encoded polypeptide is a mutant nucleic acid or polypeptide derived from any of the organisms described herein. As used herein, "derived from" refers to the source of the nucleic acid or polypeptide into which one or more mutations is introduced. For example, a polypeptide that is "derived from a plant polypeptide" refers to polypeptide of interest that results from introducing one or more mutations into the sequence of a wild-type (i.e., a sequence occurring in nature) plant polypeptide.

In some aspects, the source organism is a fungus, examples of which are species of *Aspergillus* such as *A. oryzae* and *A. niger*, species of *Saccharomyces* such as *S. cerevisiae*, species of *Schizosaccharomyces* such as *S. pombe*, and species of *Trichoderma* such as *T. reesei*. In some aspects, the source organism is a filamentous fungal cell. The term "filamentous fungi" refers to all filamentous forms of the subdivision Eumycotina (see, Alexopoulos, C. J. (1962), Introductory Mycology, Wiley, New York). These fungi are characterized by a vegetative mycelium with a cell wall composed of chitin, cellulose, and other complex polysaccharides. The filamentous fungi are morphologically, physiologically, and genetically distinct from yeasts. Vegetative growth by filamentous fungi is by hyphal elongation and carbon catabolism is obligatory aerobic. The filamentous fungal parent cell may be a cell of a species of, but not limited to, *Trichoderma*, (e.g., *Trichoderma reesei*, the asexual morph of *Hypocrea jecorina*, previously classified as *T. longibrachiatum*, *Trichoderma viride*, *Trichoderma koningii*, *Trichoderma harzianum*) (Sheir-Neirs et al., Appl. Microbiol. Biotechnol 20: 46-53, 1984; ATCC No. 56765 and ATCC No. 26921); *Penicillium* sp., *Humicola* sp. (e.g., *H. insolens*, *H. lanuginose*, or *H. grisea*); *Chrysosporium* sp. (e.g., *C. lucknowense*), *Gliocladium* sp., *Aspergillus* sp. (e.g., *A. oryzae*, *A. niger*, *A sojae*, *A. japonicus*, *A. nidulans*, or *A. awamori*) (Ward et al., Appl. Microbiol. Biotechnol. 39: 7380743, 1993 and Goedegebuur et al., Genet. 41: 89-98, 2002), *Fusarium* sp., (e.g., *F. roseum*, *F. graminum F. cerealis*, *F. oxysporuim*, or *F. venenatum*), *Neurospora* sp., (e.g., *N. crassa*), *Hypocrea* sp., *Mucor* sp., (e.g., *M. miehei*), *Rhizopus* sp. and *Emericella* sp. (see also, Innis et al., Sci. 228: 21-26, 1985). The term "*Trichoderma*" or "*Trichoderma* sp." or "*Trichoderma* spp." refer to any fungal genus previously or currently classified as *Trichoderma*.

In some aspects, the fungus is *A. nidulans*, *A. awamori*, *A. oryzae*, *A. aculeatus*, *A. niger*, *A. japonicus*, *T. reesei*, *T. viride*, *F. oxysporum*, or *F. solani*. *Aspergillus* strains are disclosed in Ward et al., Appl. Microbiol. Biotechnol. 39:738-743, 1993 and Goedegebuur et al., Curr Gene 41:89-98, 2002. In particular aspects, the fungus is a strain of *Trichoderma*, such as a strain of *T. reesei*. Strains of *T. reesei* are known and non-limiting examples include ATCC No. 13631, ATCC No. 26921, ATCC No. 56764, ATCC No. 56765, ATCC No. 56767, and NRRL 15709. In some aspects, the host strain is a derivative of RL-P37. RL-P37 is disclosed in Sheir-Neiss et al., Appl. Microbiol. Biotechnology 20:46-53, 1984.

In some aspects, the source organism is a yeast, such as *Saccharomyces* sp., *Schizosaccharomyces* sp., *Pichia* sp., or *Candida* sp.

In some aspects, the source organism is a bacterium, such as strains of *Bacillus* such as *B. licheniformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Thermosynechococcus* such as *T. elongatus*, strains of *Sinorhizobium* such as *S. meliloti*, strains of *Helicobacter* such as *H. pylori*, strains of *Agrobacterium* such as *A. tumefaciens*, strains of *Deinococcus* such as *D. radiodurans*, strains of *Listeria* such as *L. monocytogenes*, strains of *Lactobacillus* such as L. spp, or strains of *Escherichia* such as *E. coli*.

As used herein, "the genus *Bacillus*" includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*,

*B. coagulans, B. circulans, B. lautus,* and *B. thuringiensis.* It is recognized that the genus *Bacillus* continues to undergo taxonomical reorganization. Thus, it is intended that the genus include species that have been reclassified, including but not limited to such organisms as *B. stearothermophilus,* which is now named "*Geobacillus stearothermophilus.*" The production of resistant endospores in the presence of oxygen is considered the defining feature of the genus *Bacillus,* although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus.*

In some aspects, the source organism is a gram-positive bacterium. Non-limiting examples include strains of *Streptomyces* (e.g., *S. lividans, S. coelicolor,* or *S. griseus*), *Bacillus, Listeria* (e.g., *L. monocytogenes*) or *Lactobacillus* (e.g., *L.* spp). In some aspects, the source organism is a gram-negative bacterium, such as *E. coli, Pseudomonas* sp, or *H. pylori.*

In some aspects, the source organism is a plant, such as a plant from the family Fabaceae, such as the Faboideae subfamily. In some aspects, the source organism is kudzu, poplar (such as *Populus alba×tremula* CAC35696), aspen (such as *Populus tremuloides*), *Quercus robur, Arabidopsis* (such as *A. thaliana*), or *Zea* (such as *Z. mays*).

In some aspects, the source organism is an algae, such as a green algae, red algae, glaucophytes, chlorarachniophytes, euglenids, chromista, or dinoflagellates.

In some aspects, the source organism is a cyanobacterium, such such as a cyanobacterium, classified into any of the following groups based on morphology: *Chroococcales, Pleurocapsales, Oscillatoriales, Nostocales,* or *Stigonematales.* In some aspects, the cyanobacterium is *Thermosynechococcus elongates.*

Exemplary Host Cells

A variety of host cells can be used to express iron-sulfur cluster-interacting redox polypeptide, DXP pathway polypeptide (e.g., DXS, DXR, and/or IspG), DXP pathway associated polypeptide, MVA pathway polypeptide, MVA pathway associated polypeptide, PGL polypeptide or IDI polypeptide and to produce pentose sugars in the methods of the claimed invention. Exemplary host cells include cells from any of the organisms listed in the prior section under the heading "Exemplary Source Organisms." The host cell may be a cell that naturally produces isoprene or a cell that does not naturally produce isoprene. In some aspects, the host cell naturally produces pentose sugars using the DXP pathway, and one or more DXP pathway polypeptide and iron-sulfur cluster-interacting redox polypeptides are added to enhance production of pentose sugar using this pathway. In some aspects, the host cell naturally produces pentose sugars using the DXP pathway, and one or more DXP pathway nucleic acids, one or more iron-sulfur cluster-interacting redox nucleic acids, and IDI are added to enhance production of pentose sugars using this pathway.

Exemplary Transformation Methods

IspG nucleic acids, iron-sulfur cluster-interacting redox nucleic acid, DXP pathway nucleic acid, DXP pathway associated nucleic acid, or IDI nucleic acid or its vectors containing them can be inserted into a host cell (e.g., *E. coli* cell, a plant cell, a fungal cell, a yeast cell, or a bacterial cell described herein) using standard techniques known to one of skill in the art. The introduced nucleic acids may be integrated into chromosomal DNA (as described above) or maintained as extrachromosomal replicating sequences.

Exemplary Cell Culture Media and Conditions

The invention also includes a cell or a population of cells in culture that produce pentose sugar(s). By "cells in culture" is meant two or more cells in a solution (e.g., a cell medium) that allows the cells to undergo one or more cell divisions. "Cells in culture" do not include plant cells that are part of a living, multicellular plant containing cells that have differentiated into plant tissues. In various aspects, the cell culture includes at least or about 10, 20, 50, 100, 200, 500, 1,000, 5,000, 10,000 or more cells.

Carbon source that can be used to cultivate the host cells are described in WO 2009/076676, WO 2010/003007, and WO 2009/132220. In one aspect, the recombinant cells of the invention can be grown in a fed-batch culture at the 15-L scale using the following reagents:

Medium Recipe (Per Liter Fermentation Medium):

K2HPO4 7.5 g, MgSO4*7H2O 2 g, citric acid monohydrate 2 g, ferric ammonium citrate 0.3 g, yeast extract 0.5 g, 50% H2S04 2.25 mL. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 12 mL, and antibiotics were added after sterilization and pH adjustment.

1000× Trace Metal Solution (Per Liter):

Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, $H_3BO3$ 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, D-pantothenic acid 4.8 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.57 kg, Di H2O 0.38 kg, K2HPO4 7.5 g, 100% Foamblast 10 g. All components were mixed together and autoclaved. 0.82 mL 1000× Trace Metal Solution, 6.5 mLVitamin Solution and 5.5 mL Macro Salt Solution were added once the feed was cooled.

Other methods can be used to culture the recombinant cells of this invention are also described in the Examples section. Materials and methods suitable for the maintenance and growth of bacterial cultures are well known in the art. Exemplary techniques may be found in WO 2009/076676, WO 2010/003007, and WO 2009/132220, and *Manual of Methods for General Bacteriology* Gerhardt et al., eds), American Society for Microbiology, Washington, D.C. (1994) or Brock in *Biotechnology: A Textbook of Industrial Microbiology,* Second Edition (1989) Sinauer Associates, Inc., Sunderland, Mass. In some aspects, the cells are cultured in a culture medium under conditions permitting the expression of DXP pathway polypeptide (e.g., DXS, DXR, and/or IspG), iron-sulfur cluster-interacting redox polypeptide, DXP pathway associated polypeptide, or IDI polypeptide encoded by a nucleic acid inserted into the host cells.

Exemplary Methods for Decoupling Pentose Sugar Production from Cell Growth.

The recombinant cells of the invention can be grown in a way as to decouple the pentose sugar production from cell growth. When feedstock is used, it is desirable for the carbon from the feedstock to be converted to pentose sugar(s) rather than to the growth and maintenance of the cells. In some aspects, the cells are grown to a low to medium $OD_{600}$, then production of pentose sugar(s) is started or increased. This strategy permits a large portion of the carbon to be converted to pentose sugar(s). One of skill in the art can grow the recombinant cells of the invention by following the teaching in WO 2010/003007.

In some aspects, pentose sugar(s) are only produced in stationary phase. In some aspects, pentose sugar(s) is produced in both the growth phase and stationary phase. In some aspects, pentose sugar(s) is only produced in the growth phase. In some aspects, the nucleic acids encoding the various enzymes and polypeptides described herein are placed under the control of a promoter or factor that is more active in stationary phase than in the growth phase. For example, one or more iron-sulfur cluster-interacting redox nucleic acid, DXP pathway nucleic acid, DXP pathway associated nucleic acid, and/or IDI nucleic acid may be placed under control of a stationary phase sigma factor, such as RpoS. In some aspects, one or more iron-sulfur cluster-interacting redox nucleic acid, DXP pathway nucleic acid, DXP pathway associated nucleic acid, and/or IDI nucleic acid are placed under control of a promoter inducible in stationary phase, such as a promoter inducible by a response regulator active in stationary phase.

Exemplary Production of Pentose Sugar(s)

The invention provides, inter alia, compositions and methods for increasing the production of pentose sugar(s) from recombinant cells comprising (i) a heterologous nucleic acid encoding a DXS and/or DXR polypeptide and/or (ii) one or more copies of an endogenous nucleic acid encoding a DXS and/or DXR polypeptide, optionally with (iii) a heterologous nucleic acid encoding a phosphatase and/or (ii) one or more copies of an endogenous nucleic acid encoding a phosphatase. In one aspect, cultured cells using one IspG enzyme or two types of IspG enzymes, one or more DXP pathway enzymes (e.g., DXS and/or DXR), optionally in combination with iron-sulfur cluster-interacting redox genes or polypeptides, PGL genes and polypeptides, and IDI genes and polypeptides can be used. In some aspects, the recombinant cells produce a cumulative titer (total amount) of pentose sugar at greater than or about 10, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290 or 300 $g/L_{broth}$. In one aspect, 2-methylerythritol (2-ME) is produced at greater than or about 10, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290 or 300 $g/L_{broth}$. In another aspect, 1-deoxyxylulose (1-DX) is produced at greater than or about 10, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290 or 300 $g/L_{broth}$. In another aspect, monoacetylated-2-C-methylerythritol is produced at greater than or about 10, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290 or 300 $g/L_{broth}$. In another aspect, 1-DX and 2-ME are produced at greater than or about 10, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290 or 300 $g/L_{broth}$. In another aspect, 1-DX and 2-monoacetylated-2-C-methylerythritol are produced at greater than or about 10, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290 or 300 $g/L_{broth}$. In another aspect, 2-ME and 2-monoacetylated-2-C-methylerythritol are produced at greater than or about 10, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290 or 300 $g/L_{broth}$. In another aspect, 1-DX, 2-ME and monoacetylated-2-C-methylerythritol are produced at greater than or about 10, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290 or 300 $g/L_{broth}$.

In other aspects, pentose sugars such as 1-DX, 2-ME and/or monoacetylated-2-C-methylerythritol are produced with an upper limit of 10, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290 or 300 $g/L_{broth}$.

In other aspects, pentose sugars such as 1-DX, 2-ME and/or monoacetylated-2-C-methylerythritol are produced with a lower limit of 10, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290 or 300 $g/L_{broth}$.

Various measurement for pentose sugar production can be measured by methods known to one of skill in the art, for example, using GC/MS, GC/FID, NMR, and/or HPLC as exemplified herein.

The invention also contemplates cell cultures of recombinant cells that are capable of producing pentose sugars (e.g., 1-DX, 2-ME, and/or monoacetylated-2-C-methylerythritol) in any of the amount described above. Systems for producing pentose sugars using the recombinant cells described herein are also contemplated within the scope of the invention. Such system can include, but are not limited to, recombinant cells, fermentation unit(s), recovery tools and/or purification tools.

Exemplary Purification Methods

In some aspects, any of the methods described herein further include recovering the pentose sugars. In contrast to isoprene, which is mostly present in the off-gas, pentose sugars such as 2-ME, 1-DX, and monoacetylated-2-C-methylerythritol, are found in the broth. Standard techniques of recovering a biochemical from fermentation broth are known to those of skill in the art. Non-limiting examples of how to recover pentose sugars such as 2-ME, 1-DX, and monoacetylated-2-C-methylerythritol, from the fermentation broth are also described below.

EXAMPLES

The examples, which are intended to be purely exemplary of the invention and should therefore not be considered to limit the invention in any way, also describe and detail aspects and aspects of the invention discussed above. Unless indicated otherwise, temperature is in degrees Centigrade and pressure is at or near atmospheric. The foregoing examples and detailed description are offered by way of illustration and not by way of limitation. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1

Construction of Strains with an Engineered DXP Pathway that Produce 1-Deoxy-D-xylulose (1-DX) and 2-C-methyl-D-erythritol (2-ME)

Construction of Strain REM F9_17 with a Modified DXP Pathway

The isoprene producing parental strain REM D6_12 was described previously (see U.S. patent application Ser. No. 12/817,134, Example 26). The REM D6_12 strain harbors increased expression from the chromosomally encoded DXP pathway gene dxs. Using a standard electroporation method (BIO RAD), the Ptac Anabaena ispH aspA term/pEWL454 plasmid was moved into strain REM D6_12. The BIO RAD Gene Pulser system (0.1 cm cuvette cat.#165-2089) was used for the electroporation described. Transformants were recovered in LB broth for 1 hour at 37° C. before plating onto LB agar containing carbenicillin (50 μg/ml), spectinomycin (50 μg/ml) and kanamycin (50 μg/ml). The resulting strain was named REM F9_17.

Construction of Strain REM H8_12 with a Modified DXP Pathway

The REM H8_12 strain (see U.S. patent application Ser. No. 12/817,134, Example 29) was constructed from an E. coli BL21 strain that overexpressed the first two enzymes in the DXP pathway (PL.6-dxs and GI1.6-dxr, both chromosomally encoded), the last enzyme in the DXP pathway (GI1.6-yIDI, chromosomally encoded), other plasmid encoded genes involved in the DXP pathway (GI1.6-fldA-ispG/pCL, PTac-Anabaena ispH aspA term/pEWL454), the lower MVA pathway (PL.2-mKKDyI, integrated within the genome) and truncated isoprene synthase from P. alba (pDW33, plasmid encoded). The strain also contained a restored chromosomal pgl gene (t ybgS::frt). The REM H8_12 strain has increased expression of both dxs and dxr relative to the REM F9_17 strain, which is a result of varied promoter strengths governing expression of the DXP genes. Varied accumulation of dxs and dxr driven by the aforementioned promoters has been confirmed by immunoblot.

Construction of Strain REM F2_18. with a Modified DXP Pathway

The isoprene producing parental strain REM I7_11 was described previously (see U.S. patent application Ser. No. 12/817,134, example 29) was used to produce REM F2_18. The REM I7_11 strain harbors plasmid encoded copies of both fldA and ispG as well as the fldA and ispG loci present within the BL21 genome in addition to increased expression from chromosomally encoded DXP pathway genes dxs and dxr. The Ptac Anabaena ispH-T elong ispG system aspA term/pEWL454 plasmid was introduced by electroporation into strain REM I7_11. Electroporation was performed using a Bio-Rad Gene Pulser system with a 0.1 cm cuvette, cat.#165-2089. Transformation was achieved by following the manufacturer's suggested protocol. Transformants were recovered in LB broth for 1 hour at 37° C. before plating onto LB agar containing spectinomycin (50 μg/ml), carbenicillin (50 μg/ml), and kanamycin (50 μg/ml). The resulting strain was named REM F2_18.

Example 2

Fermentation of Strains with an Engineered DXP Pathway that Produce 1-Deoxy-D-xylulose and 2-C-Methyl-D-erythritol Large Scale Fermentation of the REM F9_17 Strain 2-C-Methyl-D-erythritol was produced from an E. coli strain expressing genes from the DXP pathway, grown in fed-batch culture at the 15-L scale. The following media compositions were used:

Medium Recipe (Per Liter Fermentation Medium):

K2HPO4 7.5 g, MgSO4*7H2O 2 g, citric acid monohydrate 2 g, ferric ammonium citrate 0.3 g, yeast extract 0.5 g, 50% H2S04 2.25 mL. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 12 mL, and antibiotics were added after sterilization and pH adjustment.

1000× Trace Metal Solution (Per Liter):

Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, D-pantothenic acid 4.8 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.57 kg, Di H2O 0.38 kg, K2HPO4 7.5 g, 100% Foamblast 10 g. All components were mixed together and autoclaved. 0.82 mL 1000× Trace Metal Solution, 6.5 mL Vitamin Solution and 5.5 mL Macro Salt Solution were added once the feed was cooled.

Fermentation was performed in a 15-L bioreactor with strain REMF9_17. This particular fermentation is referred to as run 20100703 (see FIG. 2). This experiment was carried out at a fermentation pH of 7.0 and temperature of 34° C. A frozen vial of the E. coli strain was thawed and inoculated into tryptone-yeast extract medium for the bioreactor. After the culture grew to optical density 1.0, measured at 550 nm ($OD_{550}$), 500 mL was used to inoculate a 15-L bioreactor and bring the initial tank volume to 5 L. The antibiotics carbenicillin, spectinomycin and kanamycin were each present at a concentration of 50 ug/mL, respectively, in the seed flask and fermentation tank.

Once the batch glucose was depleted, a glucose feed was initiated. There was an initial bolus of 3 g/min for 20 min. Afterwards the tank was pulse fed with pulses lasting 30 min. Pulses were induced by a pH rise above 7.05. Pulse rates were calculated by determining the total carbon dioxide evolution rate (mmol/h) divided by a factor of 300. The highest feed rate of glucose achieved for a given pulse was 8.2 g/min over the 50 hour fermentation.

Figure 2:
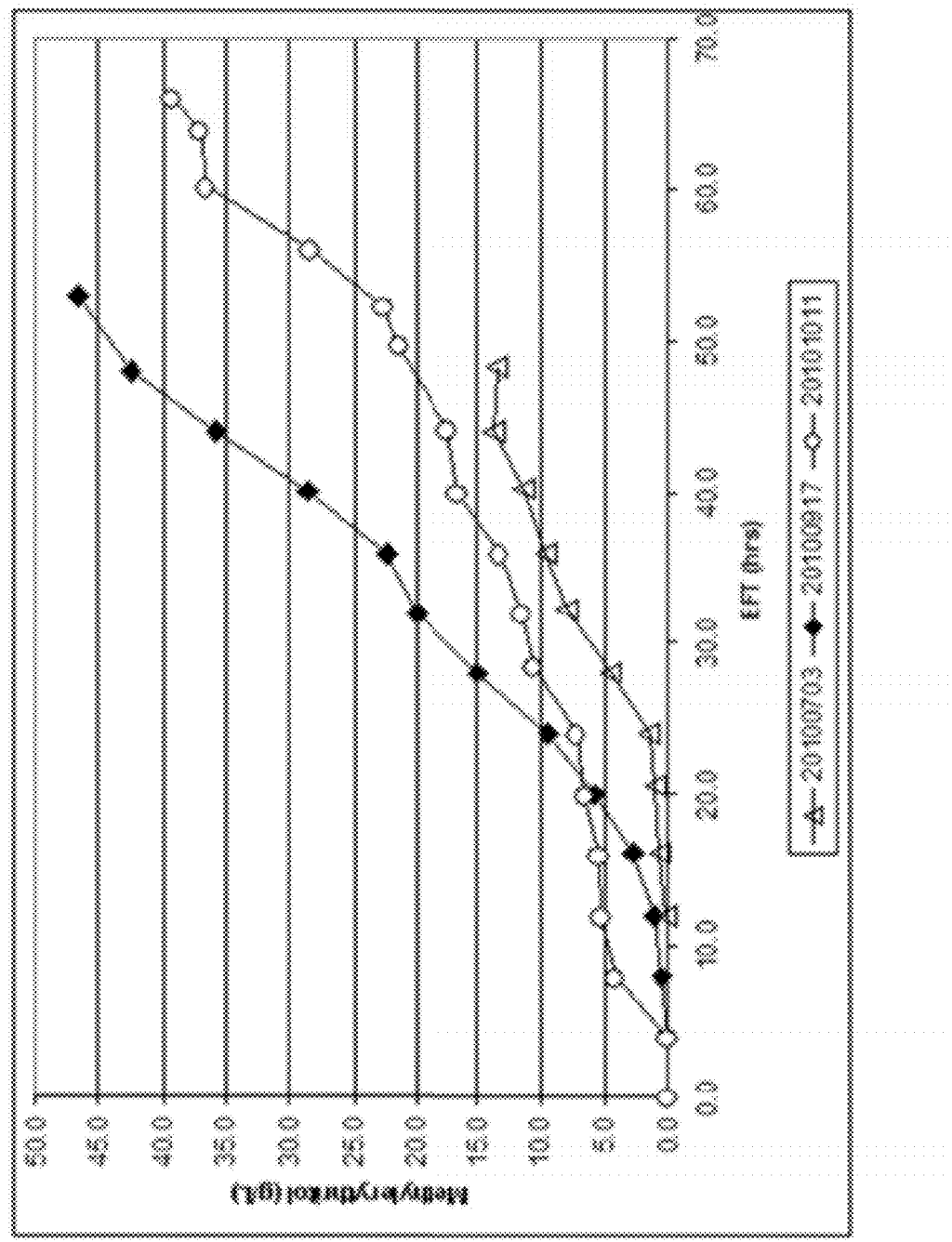
FIG. 2 shows 2-Methyl-D-erythritol (ME) titers plotted against time. Shown are the data trends for run 20100703 (open triangles), run 20100917 (black diamonds), and 20101011 (open circles). The X and Y axes are labeled in the figure.

Induction was achieved by adding isopropyl-beta-D-1-thiogalactopyranoside (IPTG) from a 10 mg/mL stock. At time zero, 3 mL was added (25 uM). Subsequent additions were at a carbon dioxide evolution rate (CER) of 25 mmol/L/h (3 mL), CER of 50 mmol/L/h (6 mL) and CER of 100 mmol/Lh (6 mL). ME titer was determined by the Organic acids column HPLC quantitation method (see method description below) and is depicted in FIG. 2.

Large Scale Fermentation of the REM H8_12 Strain

2-C-Methyl-D-erythritol was produced by an *E. coli* strain expressing genes from the DXP pathway, grown in fed-batch culture at the 15-L scale. The following media compositions were used:

Medium Recipe (Per Liter Fermentation Medium):

K2HPO4 7.5 g, MgSO4*7H2O 2 g, citric acid monohydrate 2 g, ferric ammonium citrate 0.3 g, yeast extract 0.5 g, 1000× Trace Metal Solution 1.5 ml, Macro Salt solution 3.4 mL, 50% H2S04 2.25 mL. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Mercury Vitamin Solution 12 mL, and antibiotics were added after sterilization and pH adjustment.

1000× Trace Metal Solution (Per Liter):

Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, $H_3BO3$ 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, D-pantothenic acid 4.8 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter.

Feed Solution (per Kilogram):

Glucose 0.57 kg, Di H2O 0.38 kg, K2HPO4 7.5 g, and 100% Foamblast 10 g. All components were mixed together and autoclaved.

Figure 3:
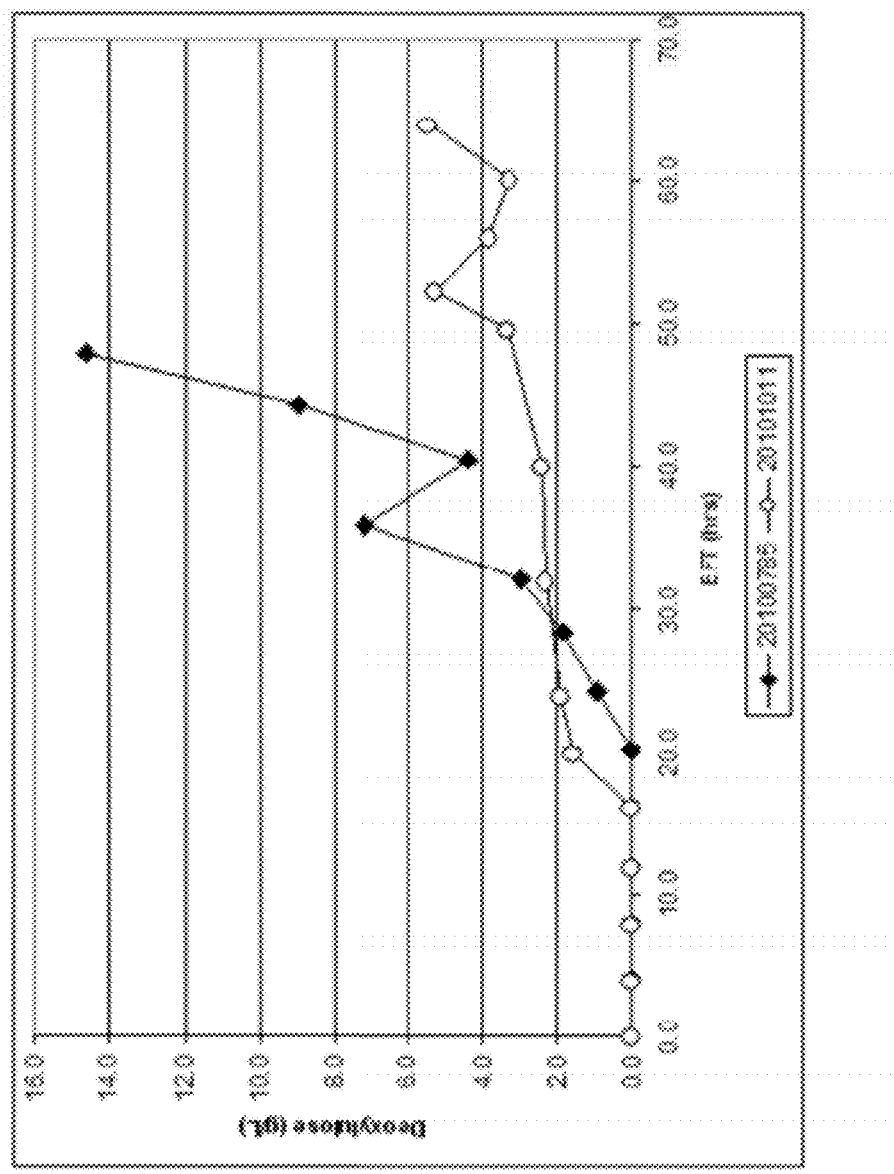
FIG. 3 shows 1-Deoxy-D-xylulose (1-DX) titers plotted against time. Shown are the data trends for run 20101011 (open circles) and run 20100785 (black diamonds). The X and Y axes are labeled in the figure.

Fermentation was performed in a 15-L bioreactor with strain REM H8_12. This particular fermentation is referred to as run 20100917 (see FIGS. 2-4). This experiment was carried out at a fermentation pH of 7.0 and temperature of 34° C. A frozen vial of the *E. coli* strain was thawed and inoculated into tryptone-yeast extract medium for the bioreactor. After the culture grew to optical density 1.0, measured at 550 nm ($OD_{550}$), 500 mL was used to inoculate a 15-L bioreactor and bring the initial tank volume to 5 L. Carbenicillin, spectinomycin and kanamycin were each present at a concentration of 50 ug/mL, respectively, in the seed flask and fermentation tank.

Once the batch glucose was depleted, the glucose feed solution was fed at an exponential rate from 0.35 g/min until the feed rate reached 2.72 g/min. This was immediately followed by a linear ramp that lasted the duration of the fermentation and brought the feed rate up to 3.75 g/min at 53 h. The total amount of glucose delivered to the bioreactor during the 53 h fermentation was 2.6 kg.

Induction was achieved by adding isopropyl-beta-D-1-thiogalactopyranoside (IPTG) from a 10 mg/mL stock. At time zero, 3 mL was added (25 uM). Subsequent additions were at a carbon dioxide evolution rate (CER) of 25 mmol/L/h (3 mL), CER of 50 mmol/L/h (6 mL) and CER of 100 mmol/Lh (6 mL).

1 L of broth was centrifuged and the supernatant was provided for methylerythritol (ME) recovery; described below. The titer of 2-ME was determined by the Organic acids column HPLC quantitation method (see FIG. 2).

Large Scale Fermentation of REM F2_18 Strain

2-C-Methyl-D-erythritol production from *E. coli* expressing genes from the DXP pathway and isoprene synthase, grown in fed-batch culture at the 15-L scale. The following media compositions were used:

Medium Recipe (Per Liter Fermentation Medium):

K2HPO4 7.5 g, MgSO4*7H2O 2 g, citric acid monohydrate 2 g, ferric ammonium citrate 0.3 g, yeast extract 0.5 g, 1000× Trace Metal Solution 1.0 ml, 50% H2S04 2.25 mL. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Mercury Vitamin Solution 8 mL, and antibiotics were added after sterilization and pH adjustment.

1000× Trace Metal Solution (Per Liter):

Citric Acids*H2O 40 g, MnSO4*H2O 30 g, NaCl 10 g, FeSO4*7H2O 1 g, $CoCl_{2*6}H2O$ 1 g, Zn504*7H2O 1 g, CuSO4*5H2O 100 mg, $H_3BO3$ 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (per Liter):

Thiamine hydrochloride 1.0 g, D-(+)-biotin 1.0 g, nicotinic acid 1.0 g, D-pantothenic acid 4.8 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.57 kg, Di H2O 0.38 kg, K2HPO4 7.5 g, and 100% Foamblast 10 g. All components were mixed together and autoclaved. Macro Salt Solution 11.1 mL, 1000× Trace Metal Solution 1.6 ml and Vitamin Solution 13.1 mL were added after the solution had cooled to 25° C.

Phosphate Solution (per Liter):

KH2PO4 68 g, K2HPO4 68 g. All components were dissolved in water, q.s. to volume and autoclaved for 30 min.

Fermentation was performed in a 15-L bioreactor with strain REM F2_18. This particular fermentation is referred to as run 20101011 (see FIGS. 2-4). This experiment was carried out at the desired fermentation pH 7.0 and temperature 34° C. A frozen vial of the *E. coli* strain was thawed and inoculated into tryptone-yeast extract medium for the bioreactor. After the culture grew to optical density 1.0, measured at 550 nm ($OD_{550}$), 500 mL was used to inoculate a 15-L bioreactor and bring the initial tank volume to 5 L. Carbenicillin, spectinomycin and kanamycin were each present at a concentration of 50 ug/mL, respectively, in the seed flask and fermentation tank.

Once the batch glucose was depleted, the glucose feed solution was fed at an exponential rate from 0.35 g/min until the feed rate reached 2.75 g/min. This was immediately followed by a linear ramp. The top rate was fixed at 4 g/min at 62.4 h EFT.

The phosphate solution described above was fed at 0.21 g/min starting at a carbon dioxide evolution rate (CER) of 50 mmol/L/h, and at 16 h feed time, was stepped down to 0.11 g/min and fed for the duration of the experiment.

Figure 4:
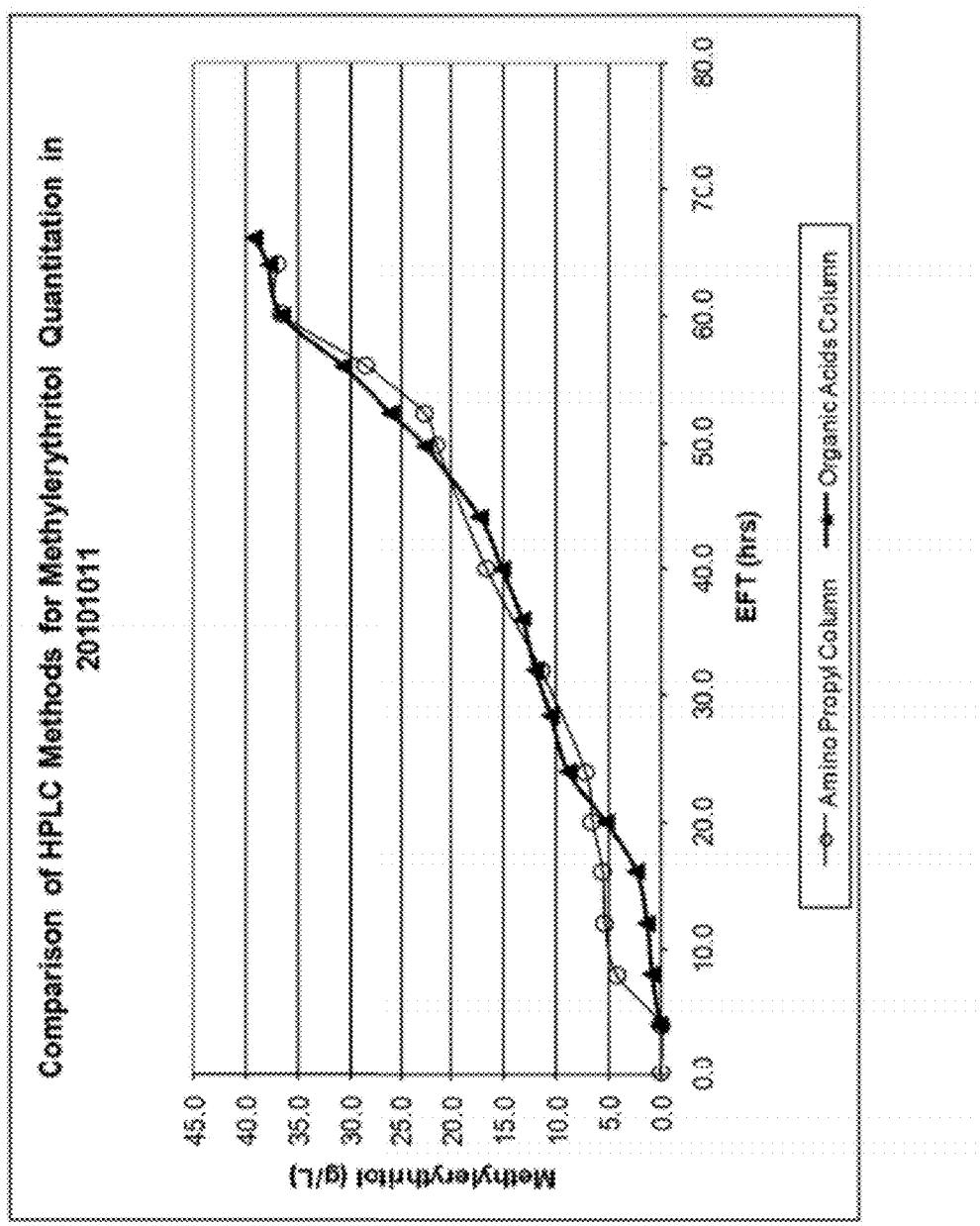
FIG. 4 shows a comparison of the values for 2-C-Methyl-D-erythritol as analyzed by the two different HPLC methods. The data shown are the values for 2-C-Methyl-D-erythritol in 20101011 as analyzed by Organic Acids Column HPLC analysis (black triangles) in comparison to the Amino Propyl Column HPLC analysis (open circles).

Induction was achieved by adding isopropyl-β-D-1-thiogalactopyranoside (IPTG) from a 10 mg/mL stock. At time zero, 3 mL was added (25 uM). Subsequent additions were at a carbon dioxide evolution rate (CER) of 25 mmol/L/h (3 mL), CER of 50 mmol/L/h (6 mL) and CER of 100 mmol/L/h (6 mL). ME titer was determined by both the Organic acids column HPLC quantitation method and the amino propyl column HPLC quantitation method described below. FIGS. 2 and 4 demonstrate the agreement in ME determination resolved by the two methods.

Large Scale Fermentation of REM I4_18

The genotype of REM I4_18 is BL21 pgl+PL.6-dxs GI1.6-dxr GI1.6-yidi PL.2-lower MVA+pDW33 (carb 50)+ Ptac-Anabaena ispH-T.elong. ispG-fd-fnr/pEWL454 (kan50). Isoprene production from *E. coli* expressing genes from the DXP pathway and isoprene synthase, grown in fed-batch culture at the 15-L scale.

Medium Recipe(Per Liter Fermentation Medium):

K2HPO4 7.5 g, MgSO4*7H2O 2 g, citric acid monohydrate 2 g, ferric ammonium citrate 0.3 g, yeast extract 0.5 g, 50% H2SO4 2.25 mL. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 12 mL, and antibiotics were added after sterilization and pH adjustment.

1000× Trace Metal Solution (Per Liter):

Citric Acids*H2O 40 g, MnSO4*H2O 30 g, NaCl 10 g, FeSO4*7H2O 1 g, CoCl2*6H2O 1 g, ZnSO4*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, D-pantothenic acid 4.8 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.57 kg, Di H2O 0.38 kg, K2HPO4 7.5 g, 100% Foamblast 10 g. All components were mixed together and autoclaved. 0.82 mL 1000× Trace Metal Solution, 6.5 mL Vitamin Solution and 5.5 mL Macro Salt Solution were added once the feed was cooled.

Fermentation was performed in a 15-L bioreactor with *E. coli* BL21 cells (strain name REM I4_18). This particular fermentation is referred to as run 20100785 (see FIG. 3).

This experiment was carried out at a fermentation pH of 7.0 and temperature of 34° C. A frozen vial of the *E. coli* strain was thawed and inoculated into tryptone-yeast extract medium for the bioreactor. After the culture grew to optical density 1.0, measured at 550 nm ($OD_{550}$), 500 mL was used to inoculate a 15-L bioreactor and bring the initial tank volume to 5 L. Carbenicillin and kanamycin were each present at a concentration of 50 ug/mL in the seed flask and fermentation tank, respectively.

Once the batch glucose was depleted, the glucose feed solution was fed. There was an initial bolus of 3 g/min for 20 min. Afterwards the tank was pulse fed with pulses lasting 30 min for 20 h. Pulses were induced by a pH rise above 7.05. Pulse rates were calculated by determining the total carbon dioxide evolution rate (mmol/h) divided by a factor between 400 and 600. After 27 h, the feed was constant at 3.5 g/min until the end of the fermentation at 51 h.

Induction was achieved by adding isopropyl-beta-D-1-thiogalactopyranoside (IPTG) from a 10 mg/mL stock. 24 mL was added (200 uM) at a carbon dioxide evolution rate of 25.

Example 3

Methods for Carbohydrate and Organic Acid Analysis

Analysis using an Aminopropyl HPLC Column

Sample Preparation and Metabolite Extraction

For the carbohydrates analysis by HPLC, fermentation broth samples were heat-treated at 65° C. for 5 minutes to lyse the cells. The samples were kept on wet ice for the remainder of the experiment. The samples were then centrifuged at 16000 RPM and −9° C. for 5 minutes. The supernatant was collected and the cell pellets were resuspended in deionized water in a volume equal to the removed supernatant. The suspension was centrifuged at 16000 RPM and −9° C. for 5 minutes. The supernatant was combined with the first collected supernatant portion, and the pellet was discarded. The samples were subject to lyophilization overnight. The lyophilized extracts were resuspended in an equal or lesser volume of 85% acetonitrile. The samples were centrifuged to remove any insoluble material and the supernatant was kept at a maximum temperature of 4° C. until the HPLC analysis.

HPLC Analytical Method

The HPLC analysis was performed using an Amino Propyl column (Phenomenex, Luna NH2-250 mm×2.0 mm×5 μm). The mobile phase was comprised of 85% Acetonitrile. 20 uL of sample was injected onto the column and run for 15 minutes isocratically with the column temperature set at 40° C. The RID (Refractive Index Detector) was used at 40° C. in positive mode to detect 2-C-methylerythritol. The peak for 2-C-methylerythritol was observed at approximately 2.3 minutes. 2-C-Methylerythritol was quantified by a standard curve generated with 2-C-methylerythritol purchased from Echelon Biosciences, Incorporated (Catalog #I-M051A). The linear standard curve generated covered a range of 0.1 g/L to 5 g/L. The limit of quantitation was observed as 0.1 g/L while the limit of detection was approximately 0.05 g/L.

Example 4

Methods for Carbohydrate and Organic Acid Analysis

Analysis Using an Organic Acids Column

Sample Preparation and Metabolite Extraction

An aliquot of 500 uL of 2% $H_2SO_4$ was added to 2 mL tubes. 167 uL of whole broth is transferred to each tube and mixed with the 2% $H_2SO_4$. Tubes were centrifuged at 14000 RPM for 5 minutes to remove cell debris. The supernatant was decanted into a 300 uL conical bottom HPLC vial and the vials were checked for air bubbles. The samples were kept at a maximum temperature of 4° C. until the HPLC analysis.

HPLC Analytical Method

The HPLC analysis was performed using an Ion Exclusion column (BioRad, Aminex HPX-87H-300 mm×7.8 mm) with a Microguard Cation guard column (BioRad, Microguard Cation H-30 mm×4.6 mm). 0.01NH$_2$SO$_4$ buffer (equivalent to 5 mM) was prepared as the mobile phase using Sulfuric Acid from Mallinckrodt Chemicals (Catalog #H378-07) and run at 0.6 mL/min. The column temperature was set to 50° C. and 20 µL of sample was injected onto the column.

Example 5

Isolation of 2-C-methyl-D-erythritol and acetylated 2-C-methyl-D-erythritols from Fermentation Broth A clarified fermentation broth sample (~1.5 L) was concentrated under reduced pressure to produce a brown oily suspension. Dilution with dichloromethane:methanol (CH$_2$Cl$_2$:MeOH) (80:20, 0.5 L) and filtration through a silica gel plug (17 cm×17 cm) was followed by further washing of the silica plug with dichloromethane:methanol (80:20, 5×1 L). The yellow filtrate was concentrated under reduced pressure to afford a brown viscous oil. Purification over a silica gel column (silica gel 200-400 mesh, 60 Å, 60 cm×6 cm) using a gradient elution (90:10 dichloromethane:methanol to 85:15 dichloromethane:methanol) afforded two products. Product #1 was a brown viscous liquid (~9 g) and was identified as consisting of a mixture of 1-O-acetyl-2-C-methyl-D-erythritol (1a) and 4-O-acetyl-2-C-methyl-D-erythritol (1b) in a 1:2 ratio by $^1$H NMR. In order to further confirm this assignment, a small sample (100 mg) of product #1 was subjected to deacetylating conditions with sodium hydride (2.6 mg, 0.11 mmol, 0.2 eq) in methanol (3 mL) at room temperature for 1 hour. This treatment produced a more polar product which co-eluted with an authentic sample of 2-C-methyl-D-erythritol (2) as determined by TLC (eluted with CH$_2$Cl$_2$/MeOH, 9:1). Product #2 was a yellow waxy solid (approximately 24 g) and had a $^1$H NMR spectrum identical to that reported in the literature.[1]

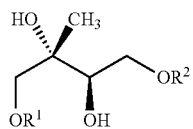

1-O-Acetyl-2-C-methyl-D-erythritol (1a) R$^1$ = COCH$_3$, R$^2$ = H
4-O-Acetyl-2-C-methyl-D-erythritol (1b) R$^1$ = H, R$^2$ = COCH$_3$
2-C-methyl-D-erythritol (2)            R$^1$ = H, R$^2$ = H 1-O-Acetyl-2-C-methyl-D-erythritol (1a): $^1$H NMR (500 MHz, D$_2$O) δ4.13, 4.02 (2H, ABq, $J_{1,1'}$=11.5 Hz, H1,1'); 3.85 (1H, dd, $J_{3,4}$=2.4 Hz, $J_{3,4'}$=11.4 Hz, H-3); 3.71 (1H, dd, $J_{3,4}$=2.4 Hz, $J_{4,4'}$=11.4 Hz, H-4); 3.58 (1H, d, $J_{4,4'}$=11.4 Hz, H-4'); 2.13 (3H, s, COCH$_3$); 1.16 (3H, s, CH$_3$).

4-O-Acetyl-2-C-methyl-D-erythritol (1b): $^1$H NMR (500 MHz, D$_2$O) δ4.38 (1H, dd, $J_{3,4}$=2.4 Hz, $J_{4,4'}$=11.4 Hz, H-4); 4.12 (1H, d, $J_{4,4'}$=11.4 Hz, H-4'); 3.86 (1H, dd, $J_{3,4'}$=2.4 Hz, $J_{3,4\infty}$=11.4 Hz, H-3); 3.60, 3.49 (2H, ABq, $J_{1,1'}$=11.5 Hz, H1,1'); 2.12 (3H, s, COCH$_3$); 1.15 (3H, s, CH$_3$).

2-C-Methyl-D-erythritol (2): $^1$H NMR (500 MHz, D$_2$O) δ3.83 (1H, dd, $J_{3,4}$=2.4 Hz, $J_{3,4'}$=11.4 Hz, H-3); 3.66 (1H, dd, $J_{3,4}$=2.4 Hz, $J_{4,4'}$=11.4 Hz, H-4); 3.60 (1H, d, $J_{4,4'}$=11.4 Hz, H-4'); 3.58, 3.47 (2H, ABq, $J_{1,1'}$=11.5 Hz, H1,1'), 1.13 (3H, s, CH$_3$).

Sakamoto, I., Ichimura, K., and Ohrui, H., *Biosci. Biotechnol. Biochem.* (2000), 64(9), 1915-1922.

Example 6

Improving Production of 2-Methyl-D-erythritol

To improve production of 2-Methyl-D-erythritol using current strains with engineered DXP pathways, various protocols are carried out.

First, further upregulation of dxs and dxr genes, with downregulation of IspDF and other genes that utilize 2-methyl-D-erythritol-5-phosphate (MEP) is done. A complete ispDF knockout is done in strains that also expressed the MVA pathway at a level sufficient to support the IPP/DMAPP levels needed to support cell growth. For example, reduced levels of ispDF is accomplished by inserting the GI1.0 promoter in place of the endogenous promoter.

Secondly, strains are run under low phosphate conditions so as to induce phosphatase expression. Phosphatases are required to convert MEP, and perhaps other DXP metabolites (cMEPP) to 2-C-methyl-D-erythritol.

Third, heterologous phosphatase (e.g. bovine phosphatase) with a sufficiently high Km so as to not disrupt normal cell metabolism is overexpressed. In some cases, this system is able to dephosphorylate pooled MEP intermediate.

Fourth, the endogenous *E. coli* phosphatases that are responsible for 2-ME production in the current strains is identified and overexpressed. The MEP phosphatase is identified via a genomic linrary or ASKA collection approach.

Fifth, the acetyl transferases responsible for converting 2-ME to the 1- and 4-monoacetyl derivatives are knocked out or downregulated to increase the yield of 2-ME. Conversely, if these monoacetates are desired, these acetyltransferases are overexpressed. In one instance, the LacA gene, a high Km acetyl)-transferase is further over expressed.

Example 7

Improving Production of 1-deoxy-D-xylulose

For improving production of 1-deoxy-D-xylulose, strategies similar to those described in Example 6 are used to improve production of 1-deoxy-D-xylulose using current strains with engineered DXP pathways except in this case, the dxr gene is knocked out or downregulated so as to accumulate 1-deoxy-D-xylulose-5-phosphate (DXP), which is subsequently dephosphorylated to 1-deoxy-D-xylulose.

What is claimed is:

1. A method of producing a pentose sugar, the method comprising:
   (a) culturing recombinant cells comprising (i) a heterologous nucleic acid encoding a 1-deoxyxylulose-5-phosphate synthase and/or 1-deoxy-D-xylulose-5-phosphate reductoisomerase polypeptide and/or (ii) more than one copy of an endogenous nucleic acid encoding a 1-deoxyxylulose-5-phosphate synthase and/or 1-deoxy-D-xylulose-5-phosphate reductoisomerase polypeptide, wherein the cells are cultured under conditions suitable for producing a pentose sugar; or
   (b) culturing recombinant cells comprising (i) a heterologous nucleic acid encoding a 1-deoxyxylulose-5-phosphate synthase and/or 1-deoxy-D-xylulose-5-phosphate reductoisomerase polypeptide and (ii) one or more copies of an endogenous nucleic acid encoding a 1-deoxyxylulose-5-phosphate synthase and/or 1-deoxy-D-xylulose-5-phosphate reductoisomerase polypeptide, wherein the cells are cultured under conditions suitable for producing a pentose sugar; and
   (c) producing said pentose sugar.

2. The method of claim 1 wherein the recombinant cells further comprise (iii) a heterologous nucleic acid encoding a phosphatase and/or (iv) one or more copies of an endogenous nucleic acid encoding a phosphatase.

3. The method of claim 2, wherein the pentose sugar is selected from the group consisting of 2-methylerythritol (2-ME) and 1-deoxyxylulose (1-DX).

4. The method of claim 3, wherein the pentose sugar is 2-methylerythritol (2-ME).

5. The method of claim 4, wherein the recombinant cells are capable of producing a cumulative titer of 2-ME of at least about 20 g/L.

6. The method of claim 4, wherein the recombinant cells are capable of producing a cumulative titer of 2-ME of at least about 30 g/L.

7. The method of claim 4, wherein the recombinant cells are capable of producing a cumulative titer of 2-ME of at least about 45 g/L.

8. The method of claim 1, wherein the recombinant cells further comprise (iii) one or more heterologous nucleic acids encoding a deoxyxylulose phosphate pathway polypeptide other than a 1-deoxyxylulose-5-phosphate synthase and/or 1-deoxy-D-xylulose-5-phosphate reductoisomerase polypeptide and/or (iv) one or more copies of an endogenous nucleic acid encoding a deoxyxylulose phosphate pathway polypeptide other than a 1-deoxyxylulose-5-phosphate synthase and/or 1-deoxy-D-xylulose-5-phosphate reductoisomerase polypeptide.

9. The method of claim 8, wherein the deoxyxylulose phosphate pathway polypeptide is 1-hydroxy-2-methyl-2-(E)-butenyl-4-diphosphate synthase.

10. The method of claim 9, wherein the 1-hydroxy-2-methyl-2-(E)-butenyl-4-diphosphate synthase polypeptide is a *T. elongatus* 1-hydroxy-2-methyl-2-(E)-butenyl-4-diphosphate synthase polypeptide.

11. The method of claim 9, wherein the 1-hydroxy-2-methyl-2-(E)-butenyl-4-diphosphate synthase polypeptide is an *E. coli* 1-hydroxy-2-methyl-2-(E)-butenyl-4-diphosphate synthase polypeptide.

12. The method of claim 8, wherein the recombinant cells further comprise a nucleic acid encoding an iron-sulfur cluster-interacting redox polypeptide.

13. The method of claim 12, wherein the iron-sulfur cluster-interacting redox polypeptide is selected from ferrodoxin and flavodoxin.

14. The method of claim 1, wherein the recombinant cells further comprise at least one heterologous nucleic acid encoding an isopentenyl-diphosphate delta-isomerase polypeptide or at least one copy of an endogenous nucleic acid encoding an isopentenyl-diphosphate delta-isomerase polypeptide.

15. The method of claim 1, wherein the recombinant cells are bacterial, algal, fungal or yeast cells.

16. The method of claim 15, wherein the cells are bacterial cells.

17. The method of claim 16, wherein the bacterial cells are gram-positive bacterial cells or gram-negative bacterial cells.

18. The method claim 17, wherein the bacterial cells are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells.

19. The method of claim 18, wherein the bacterial cells is an *E. coli* cells.

20. The method of claim 8, wherein the deoxyxylulose phosphate pathway polypeptide is selected from the group of diphosphocytidyl-2C-methyl-D-erythritol synthase, 4-diphosphocytidyl-2C-methyl-D-erythritol kinase, 2C-methyl-D-erythritol-2,4-cyclodiphosphate synthase, 1-hydroxy-2-methyl-2-(E)-butenyl-4-diphosphate reductase, and isopentenyl-diphosphate delta-isomerase.

21. The method of claim 20, wherein the additional deoxyxylulose phosphate pathway polypeptide is selected from the group of 1 hydroxy-2-methyl-2-(E)-butenyl-4-diphosphate reductase, and isopentenyl-diphosphate delta-isomerase.

22. A cell culture comprising the recombinant cells of claim 1, wherein the cell culture produces at least about 45 g/L of 2-ME.

* * * * *